United States Patent [19]
Roberts

[11] Patent Number: 6,056,690
[45] Date of Patent: May 2, 2000

[54] METHOD OF DIAGNOSING BREAST CANCER

[76] Inventor: Linda M. Roberts, 4134 N. 89th St., Milwaukee, Wis. 53222

[21] Appl. No.: 08/998,494

[22] Filed: Dec. 26, 1997

Related U.S. Application Data

[60] Provisional application No. 60/034,383, Dec. 27, 1996.

[51] Int. Cl.$^7$ ........................................ A61N 5/00
[52] U.S. Cl. ............................ 600/300; 128/920
[58] Field of Search ........................... 600/368, 300–301; 128/903, 920–925

[56] References Cited

U.S. PATENT DOCUMENTS

| | | | |
|---|---|---|---|
| 5,692,220 | 11/1997 | Diamond et al. ....................... | 600/368 |
| 5,800,347 | 9/1998 | Skates et al. ........................... | 600/300 |

*Primary Examiner*—Cary O'Connor
*Assistant Examiner*—Michael Astorino
*Attorney, Agent, or Firm*—Dorsey & Whitney LLP

[57] ABSTRACT

A method of diagnosing breast cancer by generating an inference system having a predetermined number of nodes organized into a tree of cliques. After the inference system is initialized, an evidence vector is created and initialized. The evidence vector is then customized or updated by receiving patient-specific evidence. This updated evidence vector is then propagated through the inference system to determine a breast cancer diagnosis. While determine the breast cancer diagnosis, the system can estimate the influence of each piece of patient-specific evidence on the diagnosis. Thus, the system is capable of not only determining and reporting a breast cancer diagnosis based upon patient-specific evidence, but also determining and reporting the estimated influence of each piece of patient-specific evidence considered.

24 Claims, 30 Drawing Sheets

| P(X\|Y) | $y_1$ | $y_2$ | $y_3$ |
|---|---|---|---|
| $x_1$ | $p(x_1 \mid y_1)$ | $p(x_1 \mid y_2)$ | $p(x_1 \mid y_3)$ |
| $x_2$ | $p(x_2 \mid y_1)$ | $p(x_2 \mid y_2)$ | $p(x_2 \mid y_3)$ |
| $x_3$ | $p(x_3 \mid y_1)$ | $p(x_3 \mid y_2)$ | $p(x_3 \mid y_3)$ |

FIG. 1

| P(X,Y) | $y_1$ | $y_2$ | $y_3$ |
|---|---|---|---|
| $x_1$ | $p(x_1, y_1)$ | $p(x_1, y_2)$ | $p(x_1, y_3)$ |
| $x_2$ | $p(x_2, y_1)$ | $p(x_2, y_2)$ | $p(x_2, y_3)$ |
| $x_3$ | $p(x_3, y_1)$ | $p(x_3, y_2)$ | $p(x_3, y_3)$ |

FIG. 2

| Category | Node | States |
|---|---|---|
| Diagnosis | Breast Cancer | present, absent |
| Demographic Factors | Age (years) | 20-24, 25-29, ... , 75-79 |
| | Age at Menarche (years) | <12, 12-13, >=14 |
| | Age at First Life Birth (years) | <20, 20-24, 25-29, >=30 |
| | Number of First-Degree Relatives with Breast Cancer | 0, 1, >= 2 |
| | Previous Biopsy | present, absent |
| Physical Findings | Pain | present, absent |
| | Nipple Discharge | present, absent |
| | Palpable Mass | present, absent |
| Indirect Mammographic Findings | Architectural Distortion | present, absent |
| | Asymmetry | present, absent |
| | Developing Density | present, absent |
| | Dilated Duct | present, absent |
| Direct Mammographic Findings | Mass | malignant, benign, none |
| | Mass Margin | spiculated, irregular, relatively well-defined, NA |
| | Mass Density | high, low, NA |
| | Mass Size | inSitu, <=5, 6-10, 11-20, >20, multiFocal, NA |
| | Halo Sign | present, absent, NA |
| | Tumor Location | upper outer (UO), upper inner (UI), lower outer (LO), lower inner (LI), retroareolar (RA), not available (NA) |
| | Calcification | malignant, benign, none |
| | Calcification Cluster Shape | punctate, round, linear, variable, NA |
| | Number of Calcifications in Cluster | <=5, 6-10, 11-15, 16-25, 26-50, >50, NA |
| | Calcification Shape | linear branching, irregular, indeterminate, round, NA |
| | Calcification Density | 1-2, 1-3, 2-3, 3-4, NA |
| | Calcification Arrangement | scattered, clustered, scattered & clustered, single, NA |
| | Calcification Size (mm) | 0.05-0.1, 0.05-2, 0.01-1, 0.01-2, 1-3, NA |

FIG. 4

| P(BREAST CANCER) | | AGE | MENARCHE AGE | 1ST BIRTH AGE | # OF RELATIVES |
|---|---|---|---|---|---|
| PRESENT | ABSENT | | | | |
| 0.00005100 | 0.99994900 | 20-24 | >=14 | <20 | 0 |
| 0.00013296 | 0.99986704 | | | | 1 |
| 0.00034670 | 0.99965330 | | | | 2 |
| 0.00006344 | 0.99993656 | | | 20-24 | 0 |
| 0.00013673 | 0.99986327 | | | | 1 |
| 0.00029452 | 0.99970548 | | | | 2 |
| 0.00007895 | 0.99992105 | | | 25-29 | 0 |
| 0.00014055 | 0.99985945 | | | | 1 |
| 0.00025025 | 0.99974975 | | | | 2 |
| 0.00009828 | 0.99990172 | | | >=30 | 0 |
| 0.00014453 | 0.99985547 | | | | 1 |
| 0.00021262 | 0.99978738 | | | | 2 |
| 0.00005605 | 0.99994395 | | 12-13 | <20 | 0 |
| 0.00014612 | 0.99985388 | | | | 1 |
| 0.00038102 | 0.99961898 | | | | 2 |
| 0.00006972 | 0.99993028 | | | 20-24 | 0 |
| 0.00015027 | 0.99984973 | | | | 1 |
| 0.00032368 | 0.99967632 | | | | 2 |
| 0.00008676 | 0.99991324 | | | 25-29 | 0 |
| 0.00015447 | 0.99984553 | | | | 1 |
| 0.00027503 | 0.99972497 | | | | 2 |
| 0.00010801 | 0.99989199 | | | >=30 | 0 |
| 0.00015884 | 0.99984116 | | | | 1 |
| 0.00023367 | 0.99976633 | | | | 2 |
| 0.00006156 | 0.99993844 | | <12 | <20 | 0 |
| 0.00016048 | 0.99983952 | | | | 1 |
| 0.00041846 | 0.99958154 | | | | 2 |
| 0.00007658 | 0.99992342 | | | 20-24 | 0 |
| 0.00016503 | 0.99983497 | | | | 1 |
| 0.00035549 | 0.99964451 | | | | 2 |
| 0.00009529 | 0.99990471 | | | 25-29 | 0 |
| 0.00016965 | 0.99983035 | | | | 1 |
| 0.00030206 | 0.99969794 | | | | 2 |
| 0.00011862 | 0.99988138 | | | >=30 | 0 |
| 0.00017445 | 0.99982555 | | | | 1 |
| 0.00025663 | 0.99974337 | | | | 2 |
| 0.00039604 | 0.99960396 | 25-29 | >=14 | <20 | 0 |
| 0.00103248 | 0.99896752 | | | | 1 |
| 0.00269228 | 0.99730772 | | | | 2 |
| 0.00049267 | 0.99950733 | | | 20-24 | 0 |
| 0.00106178 | 0.99893822 | | | | 1 |
| 0.00228713 | 0.99771287 | | | | 2 |

FIG. 5A

| | | | | | |
|---|---|---|---|---|---|
| 0.00061307 | 0.99938693 | | | 25-29 | 0 |
| 0.00109149 | 0.99890851 | | | | 1 |
| 0.00194337 | 0.99805663 | | | | 2 |
| 0.00076317 | 0.99923683 | | | >=30 | 0 |
| 0.00112238 | 0.99887762 | | | | 1 |
| 0.00165109 | 0.99834891 | | | | 2 |
| 0.00043525 | 0.99956475 | | 12-13 | <20 | 0 |
| 0.00113469 | 0.99886531 | | | | 1 |
| 0.00295881 | 0.99704119 | | | | 2 |
| 0.00054145 | 0.99945855 | | | 20-24 | 0 |
| 0.00116690 | 0.99883310 | | | | 1 |
| 0.00251355 | 0.99748645 | | | | 2 |
| 0.00067376 | 0.99932624 | | | 25-29 | 0 |
| 0.00119954 | 0.99880046 | | | | 1 |
| 0.00213576 | 0.99786424 | | | | 2 |
| 0.00083872 | 0.99916128 | | | >=30 | 0 |
| 0.00123349 | 0.99876651 | | | | 1 |
| 0.00181455 | 0.99818545 | | | | 2 |
| 0.00047802 | 0.99952198 | | <12 | <20 | 0 |
| 0.00124620 | 0.99875380 | | | | 1 |
| 0.00324958 | 0.99675042 | | | | 2 |
| 0.00059466 | 0.99940534 | | | 20-24 | 0 |
| 0.00128157 | 0.99871843 | | | | 1 |
| 0.00276056 | 0.99723944 | | | | 2 |
| 0.00073997 | 0.99926003 | | | 25-29 | 0 |
| 0.00131742 | 0.99868258 | | | | 1 |
| 0.00234564 | 0.99765436 | | | | 2 |
| 0.00092114 | 0.99907886 | | | >=30 | 0 |
| 0.00135471 | 0.99864529 | | | | 1 |
| 0.00199286 | 0.99800714 | | | | 2 |
| 0.00160772 | 0.99839228 | 30-34 | >=14 | <20 | 0 |
| 0.00419132 | 0.99580868 | | | | 1 |
| 0.01092926 | 0.98907074 | | | | 2 |
| 0.00200000 | 0.99800000 | | | 20-24 | 0 |
| 0.00431029 | 0.99568971 | | | | 1 |
| 0.00928457 | 0.99071543 | | | | 2 |
| 0.00248875 | 0.99751125 | | | 25-29 | 0 |
| 0.00443087 | 0.99556913 | | | | 1 |
| 0.00788907 | 0.99211093 | | | | 2 |
| 0.00309807 | 0.99690193 | | | >=30 | 0 |
| 0.00455627 | 0.99544373 | | | | 1 |
| 0.00670257 | 0.99329743 | | | | 2 |
| 0.00176688 | 0.99823312 | | 12-13 | <20 | 0 |
| 0.00460626 | 0.99539374 | | | | 1 |
| 0.01201126 | 0.98798874 | | | | 2 |
| 0.00219800 | 0.99780200 | | | 20-24 | 0 |
| 0.00473701 | 0.99526299 | | | | 1 |

FIG. 5B

| | | | | | |
|---|---|---|---|---|---|
| 0.01020374 | 0.98979626 | | | | 2 |
| 0.00273513 | 0.99726487 | | | 25-29 | 0 |
| 0.00486952 | 0.99513048 | | | | 1 |
| 0.00867009 | 0.99132991 | | | | 2 |
| 0.00340478 | 0.99659522 | | | >=30 | 0 |
| 0.00500734 | 0.99499266 | | | | 1 |
| 0.00736613 | 0.99263387 | | | | 2 |
| 0.00194051 | 0.99805949 | | <12 | <20 | 0 |
| 0.00505892 | 0.99494108 | | | | 1 |
| 0.01319162 | 0.98680838 | | | | 2 |
| 0.00241400 | 0.99758600 | | | 20-24 | 0 |
| 0.00520252 | 0.99479748 | | | | 1 |
| 0.01120647 | 0.98879353 | | | | 2 |
| 0.00300392 | 0.99699608 | | | 25-29 | 0 |
| 0.00534806 | 0.99465194 | | | | 1 |
| 0.00952210 | 0.99047790 | | | | 2 |
| 0.00373937 | 0.99626063 | | | >=30 | 0 |
| 0.00549942 | 0.99450058 | | | | 1 |
| 0.00809000 | 0.99191000 | | | | 2 |
| 0.00460829 | 0.99539171 | 35-39 | >=14 | <20 | 0 |
| 0.01201382 | 0.98798618 | | | | 1 |
| 0.03132719 | 0.96867281 | | | | 2 |
| 0.00573272 | 0.99426728 | | | 20-24 | 0 |
| 0.01235484 | 0.98764516 | | | | 1 |
| 0.02661290 | 0.97338710 | | | | 2 |
| 0.00713364 | 0.99286636 | | | 25-29 | 0 |
| 0.01270046 | 0.98729954 | | | | 1 |
| 0.02261290 | 0.97738710 | | | | 2 |
| 0.00888018 | 0.99111982 | | | >=30 | 0 |
| 0.01305991 | 0.98694009 | | | | 1 |
| 0.01921198 | 0.98078802 | | | | 2 |
| 0.00506452 | 0.99493548 | | 12-13 | <20 | 0 |
| 0.01320319 | 0.98679681 | | | | 1 |
| 0.03442858 | 0.96557142 | | | | 2 |
| 0.00630026 | 0.99369974 | | | 20-24 | 0 |
| 0.01357797 | 0.98642203 | | | | 1 |
| 0.02924758 | 0.97075242 | | | | 2 |
| 0.00783987 | 0.99216013 | | | 25-29 | 0 |
| 0.01395781 | 0.98604219 | | | | 1 |
| 0.02485158 | 0.97514842 | | | | 2 |
| 0.00975932 | 0.99024068 | | | >=30 | 0 |
| 0.01435284 | 0.98564716 | | | | 1 |
| 0.02111397 | 0.97888603 | | | | 2 |
| 0.00556221 | 0.99443779 | | <12 | <20 | 0 |
| 0.01450069 | 0.98549931 | | | | 1 |
| 0.03781192 | 0.96218808 | | | | 2 |
| 0.00691939 | 0.99308061 | | | 20-24 | 0 |

FIG. 5C

| | | | | | |
|---|---|---|---|---|---|
| 0.01491229 | 0.98508771 | | | | 1 |
| 0.03212177 | 0.96787823 | | | | 2 |
| 0.00861030 | 0.99138970 | | | 25-29 | 0 |
| 0.01532946 | 0.98467054 | | | | 1 |
| 0.02729377 | 0.97270623 | | | | 2 |
| 0.01071838 | 0.98928162 | | | >=30 | 0 |
| 0.01576331 | 0.98423669 | | | | 1 |
| 0.02318886 | 0.97681114 | | | | 2 |
| 0.01075269 | 0.98924731 | 40-44 | >=14 | <20 | 0 |
| 0.02803226 | 0.97196774 | | | | 1 |
| 0.07309677 | 0.92690323 | | | | 2 |
| 0.01337634 | 0.98662366 | | | 20-24 | 0 |
| 0.02882796 | 0.97117204 | | | | 1 |
| 0.06209677 | 0.93790323 | | | | 2 |
| 0.01664516 | 0.98335484 | | | 25-29 | 0 |
| 0.02963441 | 0.97036559 | | | | 1 |
| 0.05276344 | 0.94723656 | | | | 2 |
| 0.02072043 | 0.97927957 | | | >=30 | 0 |
| 0.03047312 | 0.96952688 | | | | 1 |
| 0.04482796 | 0.95517204 | | | | 2 |
| 0.01181720 | 0.98818280 | | 12-13 | <20 | 0 |
| 0.03080745 | 0.96919255 | | | | 1 |
| 0.08033335 | 0.91966665 | | | | 2 |
| 0.01470060 | 0.98529940 | | | 20-24 | 0 |
| 0.03168192 | 0.96831808 | | | | 1 |
| 0.06824435 | 0.93175565 | | | | 2 |
| 0.01829303 | 0.98170697 | | | 25-29 | 0 |
| 0.03256822 | 0.96743178 | | | | 1 |
| 0.05798702 | 0.94201298 | | | | 2 |
| 0.02277175 | 0.97722825 | | | >=30 | 0 |
| 0.03348996 | 0.96651004 | | | | 1 |
| 0.04926592 | 0.95073408 | | | | 2 |
| 0.01297849 | 0.98702151 | | <12 | <20 | 0 |
| 0.03383494 | 0.96616506 | | | | 1 |
| 0.08822781 | 0.91177219 | | | | 2 |
| 0.01614525 | 0.98385475 | | | 20-24 | 0 |
| 0.03479534 | 0.96520466 | | | | 1 |
| 0.07495081 | 0.92504919 | | | | 2 |
| 0.02009071 | 0.97990929 | | | 25-29 | 0 |
| 0.03576873 | 0.96423127 | | | | 1 |
| 0.06368547 | 0.93631453 | | | | 2 |
| 0.02500956 | 0.97499044 | | | >=30 | 0 |
| 0.03678105 | 0.96321895 | | | | 1 |
| 0.05410734 | 0.94589266 | | | | 2 |
| 0.02000000 | 0.98000000 | 45-49 | >=14 | <20 | 0 |
| 0.05214000 | 0.94786000 | | | | 1 |
| 0.13596000 | 0.86404000 | | | | 2 |

FIG. 5D

|  |  |  |  |  |  |
|---|---|---|---|---|---|
| 0.02488000 | 0.97512000 |  |  | 20-24 | 0 |
| 0.05362000 | 0.94638000 |  |  |  | 1 |
| 0.11550000 | 0.88450000 |  |  |  | 2 |
| 0.03096000 | 0.96904000 |  |  | 25-29 | 0 |
| 0.05512000 | 0.94488000 |  |  |  | 1 |
| 0.09814000 | 0.90186000 |  |  |  | 2 |
| 0.03854000 | 0.96146000 |  |  | >=30 | 0 |
| 0.05668000 | 0.94332000 |  |  |  | 1 |
| 0.08338000 | 0.91662000 |  |  |  | 2 |
| 0.02198000 | 0.97802000 |  | 12-13 | <20 | 0 |
| 0.05730186 | 0.94269814 |  |  |  | 1 |
| 0.14942004 | 0.85057996 |  |  |  | 2 |
| 0.02734312 | 0.97265688 |  |  | 20-24 | 0 |
| 0.05892838 | 0.94107162 |  |  |  | 1 |
| 0.12693450 | 0.87306550 |  |  |  | 2 |
| 0.03402504 | 0.96597496 |  |  | 25-29 | 0 |
| 0.06057688 | 0.93942312 |  |  |  | 1 |
| 0.10785586 | 0.89214414 |  |  |  | 2 |
| 0.04235546 | 0.95764454 |  |  | >=30 | 0 |
| 0.06229132 | 0.93770868 |  |  |  | 1 |
| 0.09163462 | 0.90836538 |  |  |  | 2 |
| 0.02414000 | 0.97586000 |  | <12 | <20 | 0 |
| 0.06293298 | 0.93706702 |  |  |  | 1 |
| 0.16410372 | 0.83589628 |  |  |  | 2 |
| 0.03003016 | 0.96996984 |  |  | 20-24 | 0 |
| 0.06471934 | 0.93528066 |  |  |  | 1 |
| 0.13940850 | 0.86059150 |  |  |  | 2 |
| 0.03736872 | 0.96263128 |  |  | 25-29 | 0 |
| 0.06652984 | 0.93347016 |  |  |  | 1 |
| 0.11845498 | 0.88154502 |  |  |  | 2 |
| 0.04651778 | 0.95348222 |  |  | >=30 | 0 |
| 0.06841276 | 0.93158724 |  |  |  | 1 |
| 0.10063966 | 0.89936034 |  |  |  | 3 |
| 0.03030303 | 0.96969697 | 50-54 | >=14 | <20 | 0 |
| 0.07900000 | 0.92100000 |  |  |  | 1 |
| 0.20600000 | 0.79400000 |  |  |  | 2 |
| 0.03769697 | 0.96230303 |  |  | 20-24 | 0 |
| 0.08124242 | 0.91875758 |  |  |  | 1 |
| 0.17500000 | 0.82500000 |  |  |  | 2 |
| 0.04690909 | 0.95309091 |  |  | 25-29 | 0 |
| 0.08351515 | 0.91648485 |  |  |  | 1 |
| 0.14869697 | 0.85130303 |  |  |  | 2 |
| 0.05839394 | 0.94160606 |  |  | >=30 | 0 |
| 0.08587879 | 0.91412121 |  |  |  | 1 |
| 0.12633333 | 0.87366667 |  |  |  | 2 |
| 0.03330303 | 0.96669697 |  | 12-13 | <20 | 0 |
| 0.08682100 | 0.91317900 |  |  |  | 1 |

FIG. 5E

| | | | | | |
|---|---|---|---|---|---|
| 0.22639400 | 0.77360600 | | | | 2 |
| 0.04142897 | 0.95857103 | | | 20-24 | 0 |
| 0.08928542 | 0.91071458 | | | | 1 |
| 0.19232500 | 0.80767500 | | | | 2 |
| 0.05155309 | 0.94844691 | | | 25-29 | 0 |
| 0.09178315 | 0.90821685 | | | | 1 |
| 0.16341797 | 0.83658203 | | | | 2 |
| 0.06417494 | 0.93582506 | | | >=30 | 0 |
| 0.09438079 | 0.90561921 | | | | 1 |
| 0.13884033 | 0.86115967 | | | | 2 |
| 0.03657576 | 0.96342424 | | <12 | <20 | 0 |
| 0.09535300 | 0.90464700 | | | | 1 |
| 0.24864200 | 0.75135800 | | | | 2 |
| 0.04550024 | 0.95449976 | | | 20-24 | 0 |
| 0.09805961 | 0.90194039 | | | | 1 |
| 0.21122500 | 0.78877500 | | | | 2 |
| 0.05661927 | 0.94338073 | | | 25-29 | 0 |
| 0.10080279 | 0.89919721 | | | | 1 |
| 0.17947724 | 0.82052276 | | | | 2 |
| 0.070481 | 0.929519 | | | >=30 | 0 |
| 0.103655 | 0.896345 | | | | 1 |
| 0.15248433 | 0.84751567 | | | | 2 |
| 0.04166667 | 0.95833333 | 55-59 | >=14 | <20 | 0 |
| 0.10862500 | 0.89137500 | | | | 1 |
| 0.28325000 | 0.71675000 | | | | 2 |
| 0.05183333 | 0.94816667 | | | 20-24 | 0 |
| 0.11170833 | 0.88829167 | | | | 1 |
| 0.24062500 | 0.75937500 | | | | 2 |
| 0.06450000 | 0.93550000 | | | 25-29 | 0 |
| 0.11483333 | 0.88516667 | | | | 1 |
| 0.20445833 | 0.79554167 | | | | 2 |
| 0.08029167 | 0.91970833 | | | >=30 | 0 |
| 0.11808333 | 0.88191667 | | | | 1 |
| 0.17370833 | 0.82629167 | | | | 2 |
| 0.04579167 | 0.95420833 | | 12-13 | <20 | 0 |
| 0.11937887 | 0.88062113 | | | | 1 |
| 0.31129175 | 0.68870825 | | | | 2 |
| 0.05696483 | 0.94303517 | | | 20-24 | 0 |
| 0.12276746 | 0.87723254 | | | | 1 |
| 0.26444687 | 0.73555313 | | | | 2 |
| 0.07088550 | 0.92911450 | | | 25-29 | 0 |
| 0.12620183 | 0.87379817 | | | | 1 |
| 0.22469971 | 0.77530029 | | | | 2 |
| 0.08824054 | 0.91175946 | | | >=30 | 0 |
| 0.12977358 | 0.87022642 | | | | 1 |
| 0.19090546 | 0.80909454 | | | | 2 |
| 0.05029167 | 0.94970833 | | <12 | <20 | 0 |

FIG. 5F

| | | | | | |
|---|---|---|---|---|---|
| 0.13111038 | 0.86888962 | | | | 1 |
| 0.34188275 | 0.65811725 | | | | 2 |
| 0.06256283 | 0.93743717 | | | 20-24 | 0 |
| 0.13483196 | 0.86516804 | | | | 1 |
| 0.29043438 | 0.70956562 | | | | 2 |
| 0.07785150 | 0.92214850 | | | 25-29 | 0 |
| 0.13860383 | 0.86139617 | | | | 1 |
| 0.24678121 | 0.75321879 | | | | 2 |
| 0.09691204 | 0.90308796 | | | >=30 | 0 |
| 0.14252658 | 0.85747342 | | | | 1 |
| 0.20966596 | 0.79033404 | | | | 2 |
| 0.05882353 | 0.94117647 | 60-64 | >=14 | <20 | 0 |
| 0.15335294 | 0.84664706 | | | | 1 |
| 0.39988235 | 0.60011765 | | | | 2 |
| 0.07317647 | 0.92682353 | | | 20-24 | 0 |
| 0.15770588 | 0.84229412 | | | | 1 |
| 0.33970588 | 0.66029412 | | | | 2 |
| 0.09105882 | 0.90894118 | | | 25-29 | 0 |
| 0.16211765 | 0.83788235 | | | | 1 |
| 0.28864706 | 0.71135294 | | | | 2 |
| 0.11335294 | 0.88664706 | | | >=30 | 0 |
| 0.16670588 | 0.83329412 | | | | 1 |
| 0.24523529 | 0.75476471 | | | | 2 |
| 0.06464706 | 0.93535294 | | 12-13 | <20 | 0 |
| 0.16853488 | 0.83146512 | | | | 1 |
| 0.43947071 | 0.56052929 | | | | 2 |
| 0.08042094 | 0.91957906 | | | 20-24 | 0 |
| 0.17331876 | 0.82668124 | | | | 1 |
| 0.37333676 | 0.62666324 | | | | 2 |
| 0.10007365 | 0.89992635 | | | 25-29 | 0 |
| 0.17816729 | 0.82183271 | | | | 1 |
| 0.31722312 | 0.68277688 | | | | 2 |
| 0.12457488 | 0.87542512 | | | >=30 | 0 |
| 0.18320976 | 0.81679024 | | | | 1 |
| 0.26951359 | 0.73048641 | | | | 2 |
| 0.07100000 | 0.92900000 | | <12 | <20 | 0 |
| 0.18509700 | 0.81490300 | | | | 1 |
| 0.48265800 | 0.51734200 | | | | 2 |
| 0.08832400 | 0.91167600 | | | 20-24 | 0 |
| 0.19035100 | 0.80964900 | | | | 1 |
| 0.41002500 | 0.58997500 | | | | 2 |
| 0.10990800 | 0.89009200 | | | 25-29 | 0 |
| 0.19567600 | 0.80432400 | | | | 1 |
| 0.34839700 | 0.65160300 | | | | 2 |
| 0.13681700 | 0.86318300 | | | >=30 | 0 |
| 0.20121400 | 0.79878600 | | | | 1 |
| 0.29599900 | 0.70400100 | | | | 2 |

FIG. 5G

| | | | | | |
|---|---|---|---|---|---|
| 0.07142857 | 0.92857143 | 65-69 | >=14 | <20 | 0 |
| 0.18621429 | 0.81378571 | | | | 1 |
| 0.48557143 | 0.51442857 | | | | 2 |
| 0.08885714 | 0.91114286 | | | 20-24 | 0 |
| 0.19150000 | 0.80850000 | | | | 1 |
| 0.41250000 | 0.58750000 | | | | 2 |
| 0.11057143 | 0.88942857 | | | 25-29 | 0 |
| 0.19685714 | 0.80314286 | | | | 1 |
| 0.35050000 | 0.64950000 | | | | 2 |
| 0.13764286 | 0.86235714 | | | >=30 | 0 |
| 0.20242857 | 0.79757143 | | | | 1 |
| 0.29778571 | 0.70221429 | | | | 2 |
| 0.07850000 | 0.92150000 | | 12-13 | <20 | 0 |
| 0.20464950 | 0.79535050 | | | | 1 |
| 0.53364300 | 0.46635700 | | | | 2 |
| 0.09765400 | 0.90234600 | | | 20-24 | 0 |
| 0.21045850 | 0.78954150 | | | | 1 |
| 0.45333750 | 0.54666250 | | | | 2 |
| 0.12151800 | 0.87848200 | | | 25-29 | 0 |
| 0.21634600 | 0.78365400 | | | | 1 |
| 0.38519950 | 0.61480050 | | | | 2 |
| 0.15126950 | 0.84873050 | | | >=30 | 0 |
| 0.22246900 | 0.77753100 | | | | 1 |
| 0.32726650 | 0.67273350 | | | | 2 |
| 0.08621429 | 0.91378571 | | <12 | <20 | 0 |
| 0.22476064 | 0.77523936 | | | | 1 |
| 0.58608471 | 0.41391529 | | | | 2 |
| 0.10725057 | 0.89274943 | | | 20-24 | 0 |
| 0.23114050 | 0.76885950 | | | | 1 |
| 0.49788750 | 0.50211250 | | | | 2 |
| 0.13345971 | 0.86654029 | | | 25-29 | 0 |
| 0.23760657 | 0.76239343 | | | | 1 |
| 0.42305350 | 0.57694650 | | | | 2 |
| 0.16613493 | 0.83386507 | | | >=30 | 0 |
| 0.24433129 | 0.75566871 | | | | 1 |
| 0.35942736 | 0.64057264 | | | | 2 |
| 0.09090909 | 0.90909091 | 70-74 | >=14 | <20 | 0 |
| 0.23700000 | 0.76300000 | | | | 1 |
| 0.61800000 | 0.38200000 | | | | 2 |
| 0.11309091 | 0.88690909 | | | 20-24 | 0 |
| 0.24372727 | 0.75627273 | | | | 1 |
| 0.52500000 | 0.47500000 | | | | 2 |
| 0.14072727 | 0.85927273 | | | 25-29 | 0 |
| 0.25054545 | 0.74945455 | | | | 1 |
| 0.44609091 | 0.55390909 | | | | 2 |
| 0.17518182 | 0.82481818 | | | >=30 | 0 |
| 0.25763636 | 0.74236364 | | | | 1 |

FIG. 5H

| | | | | | |
|---|---|---|---|---|---|
| 0.37900000 | 0.62100000 | | | | 2 |
| 0.09990909 | 0.90009091 | | 12-13 | <20 | 0 |
| 0.26046300 | 0.73953700 | | | | 1 |
| 0.67918200 | 0.32081800 | | | | 2 |
| 0.12428691 | 0.87571309 | | | 20-24 | 0 |
| 0.26785627 | 0.73214373 | | | | 1 |
| 0.57697500 | 0.42302500 | | | | 2 |
| 0.15465927 | 0.84534073 | | | 25-29 | 0 |
| 0.27534945 | 0.72465055 | | | | 1 |
| 0.49025391 | 0.50974609 | | | | 2 |
| 0.19252482 | 0.80747518 | | | >=30 | 0 |
| 0.28314236 | 0.71685764 | | | | 1 |
| 0.41652100 | 0.58347900 | | | | 2 |
| 0.10972727 | 0.89027273 | | <12 | <20 | 0 |
| 0.28605900 | 0.71394100 | | | | 1 |
| 0.74592600 | 0.25407400 | | | | 2 |
| 0.13650073 | 0.86349927 | | | 20-24 | 0 |
| 0.29417882 | 0.70582118 | | | | 1 |
| 0.63367500 | 0.36632500 | | | | 2 |
| 0.16985782 | 0.83014218 | | | 25-29 | 0 |
| 0.30240836 | 0.69759164 | | | | 1 |
| 0.53843173 | 0.46156827 | | | | 2 |
| 0.21144445 | 0.78855555 | | | >=30 | 0 |
| 0.31096709 | 0.68903291 | | | | 1 |
| 0.45745300 | 0.54254700 | | | | 2 |
| 0.10000000 | 0.90000000 | 75-79 | >=14 | <20 | 0 |
| 0.26070000 | 0.73930000 | | | | 1 |
| 0.67980000 | 0.32020000 | | | | 2 |
| 0.12440000 | 0.87560000 | | | 20-24 | 0 |
| 0.26810000 | 0.73190000 | | | | 1 |
| 0.57750000 | 0.42250000 | | | | 2 |
| 0.15480000 | 0.84520000 | | | 25-29 | 0 |
| 0.27560000 | 0.72440000 | | | | 1 |
| 0.49070000 | 0.50930000 | | | | 2 |
| 0.19270000 | 0.80730000 | | | >=30 | 0 |
| 0.28340000 | 0.71660000 | | | | 1 |
| 0.41690000 | 0.58310000 | | | | 2 |
| 0.10990000 | 0.89010000 | | 12-13 | <20 | 0 |
| 0.28650930 | 0.71349070 | | | | 1 |
| 0.74710020 | 0.25289980 | | | | 2 |
| 0.13671560 | 0.86328440 | | | 20-24 | 0 |
| 0.29464190 | 0.70535810 | | | | 1 |
| 0.63467250 | 0.36532750 | | | | 2 |
| 0.17012520 | 0.82987480 | | | 25-29 | 0 |
| 0.30288440 | 0.69711560 | | | | 1 |
| 0.53927930 | 0.46072070 | | | | 2 |
| 0.21177730 | 0.78822270 | | | >=30 | 0 |

FIG. 5I

| | | | | | |
|---|---|---|---|---|---|
| 0.31145660 | 0.68854340 | | | | 1 |
| 0.45817310 | 0.54182690 | | | | 2 |
| 0.12070000 | 0.87930000 | | <12 | <20 | 0 |
| 0.31466490 | 0.68533510 | | | | 1 |
| 0.82051860 | 0.17948140 | | | | 2 |
| 0.15015080 | 0.84984920 | | | 20-24 | 0 |
| 0.32359670 | 0.67640330 | | | | 1 |
| 0.69704250 | 0.30295750 | | | | 2 |
| 0.18684360 | 0.81315640 | | | 25-29 | 0 |
| 0.33264920 | 0.66735080 | | | | 1 |
| 0.59227490 | 0.40772510 | | | | 2 |
| 0.23258890 | 0.76741110 | | | >=30 | 0 |
| 0.34206380 | 0.65793620 | | | | 1 |
| 0.50319830 | 0.49680170 | | | | 2 |

FIG. 5J

| P(AGE) | AGE-RANGE IN YEARS |
|---|---|
| 0.1025 | 20-24 |
| 0.1107 | 25-29 |
| 0.1235 | 30-34 |
| 0.1185 | 35-39 |
| 0.1067 | 40-44 |
| 0.0874 | 45-49 |
| 0.0706 | 50-54 |
| 0.0616 | 55-59 |
| 0.0610 | 60-64 |
| 0.0612 | 65-69 |
| 0.0536 | 70-74 |
| 0.0427 | 75-79 |

FIG. 6

| P(AGE OF MENARCHE) | AGE-RANGE IN YEARS |
|---|---|
| 0.350 | >=14 |
| 0.514 | 12-13 |
| 0.136 | <12 |

FIG. 7

| P(AGE OF FIRST BIRTH) | AGE RANGE IN YEARS |
|---|---|
| 0.2595 | <20 |
| 0.374 | 20-24 |
| 0.255 | 25-29 |
| 0.1115 | >=30 |

FIG. 8

| P(NUMBER OF RELATIVES) | NUMBER OF RELATIVES |
|---|---|
| 0.6 | 0 |
| 0.3 | 1 |
| 0.1 | >=2 |

FIG. 9

| P(PREVIOUS BIOPSY) | STATE |
|---|---|
| 0.2 | PRESENT |
| 0.8 | ABSENT |

FIG. 10

| P(ARCHITECTURAL DISTORTION) | | BREAST CANCER STATE | PREVIOUS BIOPSY STATE |
|---|---|---|---|
| PRESENT | ABSENT | | |
| 99/100 | 1/100 | PRESENT | PRESENT |
| 26/300 | 274/300 | PRESENT | ABSENT |
| 99/100 | 1/100 | ABSENT | PRESENT |
| 1/1000 | 999/1000 | ABSENT | ABSENT |

FIG. 11

| P(ASYMMETRY) | | BREAST CANCER STATE |
|---|---|---|
| PRESENT | ABSENT | |
| 8/300 | 292/300 | PRESENT |
| 1/1000 | 999/1000 | ABSENT |

FIG. 12

| P(DEVELOPING DENSITY) | | BREAST CANCER STATE |
|---|---|---|
| PRESENT | ABSENT | |
| 19/300 | 281/300 | PRESENT |
| 1/1000 | 999/1000 | ABSENT |

FIG. 13

| P(DILATED DUCT) | | BREAST CANCER STATE |
|---|---|---|
| PRESENT | ABSENT | |
| 4/57 | 53/57 | PRESENT |
| 1/100 | 99/100 | ABSENT |

FIG. 14

| P(MASS) | | | BREAST CANCER STATE |
|---|---|---|---|
| MALIGNANT | BENIGN | NONE | |
| 0.40 | 0.0 | 0.60 | PRESENT |
| 0.0 | 0.1 | 0.9 | ABSENT |

FIG. 15

| P(CALCIFICATION) | | | BREAST CANCER STATE |
|---|---|---|---|
| MALIGNANT | BENIGN | NONE | |
| 0.20 | 0.0 | 0.80 | PRESENT |
| 0.0 | 0.1 | 0.9 | ABSENT |

FIG. 16

| P(TUMOR LOCATION) | | | | | | MASS STATE |
|---|---|---|---|---|---|---|
| UO | UI | LO | LI | RA | NA | |
| 0.52 | 0.143 | 0.143 | 0.05 | 0.144 | 0.00 | MALIGNANT |
| 0.54 | 0.14 | 0.10 | 0.07 | 0.15 | 0.00 | BENIGN |
| 0.00 | 0.0 | 0.00 | 0.00 | 0.00 | 1.00 | NONE |

FIG. 17

| P(MASS MARGIN) | | | | MASS STATE |
|---|---|---|---|---|
| SPICULATED | IRREGULAR | RWDEFINED | NA | |
| 49/118 | 57/118 | 12/118 | 0.0 | MALIGNANT |
| 1/1000 | 1/1000 | 998/100 | 0.0 | BENIGN |
| 0 | 0.0 | 0.0 | 1.0 | NONE |

FIG. 18

| P(MASS DENSITY) | | | MASS STATE |
|---|---|---|---|
| LOW DENSITY | HIGH DENSITY | NA | |
| 21/40 | 19/40 | 0.0 | MALIGNANT |
| 41/51 | 10/51 | 0.0 | BENIGN |
| 0.0 | 0.0 | 1.0 | NONE |

FIG. 19

| P(HALO SIGN) | | | MASS STATE |
|---|---|---|---|
| PRESENT | ABSENT | NA | |
| 25/1000 | 975/1000 | 0 | MALIGNANT |
| 0.3 | 0.7 | 0 | BENIGN |
| 0 | 0 | 1 | NONE |

FIG. 20

| P(MASS SIZE) | | | | | | | MASS STATE |
|---|---|---|---|---|---|---|---|
| INSITU | <=5 | 6-10 | 11-20 | >20 | MULTIFOCAL | NA | |
| 84/300 | 20/300 | 78/300 | 67/300 | 7/300 | 44/300 | 0 | MALIGNANT |
| 8/200 | 60/200 | 10/200 | 14/200 | 90/200 | 18/200 | 0 | BENIGN |
| 0 | 0 | 0 | 0 | 0 | 0 | 1 | NONE |

FIG. 21

| P(CALCIFICATION SHAPE) | | | | | CALCIFICATION STATE |
|---|---|---|---|---|---|
| LINEAR BRANCHING | IRREGULAR | INDETERMINATE | ROUND | NA | |
| 68/125 | 8/125 | 49/125 | 0.0 | 0.0 | MALIGNANT |
| 1/100 | 1/100 | 1/100 | 97/100 | 0.0 | BENIGN |
| 0.0 | 0.0 | 0.0 | 0.0 | 0.0 | NONE |

FIG. 22

| P(NUMBER IN CLUSTER) | | | | | | | CALCIFICATION STATE |
|---|---|---|---|---|---|---|---|
| <=5 | 6-10 | 11-15 | 16-25 | 26-50 | >50 | NA | |
| 0 | 0.16 | 0.14 | 0.20 | 0.32 | 0.18 | 0.0 | MALIGNANT |
| 0.04 | 0.42 | 0.30 | 0.10 | 0.02 | 0.12 | 0.0 | BENIGN |
| 0.0 | 0.0 | 0.0 | 0.0 | 0.0 | 0.0 | 1.0 | NONE |

FIG. 23

| P(CALCIFICATION CLUSTER SHAPE) | | | | | CALCIFICATION STATE |
|---|---|---|---|---|---|
| PUNCTATE | ROUND | LINEAR | VARIABLE | NA | |
| 0.36 | 0.08 | 0.02 | 0.54 | 0.0 | MALIGNANT |
| 0.64 | 0.14 | 0.04 | 0.18 | 0.0 | BENIGN |
| 0.0 | 0.0 | 0.0 | 0.0 | 1.0 | NONE |

FIG. 24

| P(CALCIFICATION DENSITY) | | | | | CALCIFICATION STATE |
|---|---|---|---|---|---|
| 1-2 | 1-3 | 2-3 | 3-4 | NA | |
| 0.18 | 0.76 | 0.04 | 0.02 | 0.0 | MALIGNANT |
| 0.12 | 0.48 | 0.26 | 0.14 | 0.0 | BENIGN |
| 0.0 | 0.0 | 0.0 | 0.0 | 1.0 | NONE |

FIG. 25

| P(CALCIFICATION SIZE) | | | | | | CALCIFICATION STATE |
|---|---|---|---|---|---|---|
| 0.05-0.1 | 0.05-2 | 0.01-1 | 0.01-2 | 1-3 | NA | |
| 0.29 | 0.33 | 0.28 | 0.10 | 0.00 | 0.0 | MALIGNANT |
| 0.12 | 0.10 | 0.75 | 0.06 | 0.02 | 0.0 | BENIGN |
| 0.0 | 0.0 | 0.0 | 0.0 | 0.0 | 1.0 | NONE |

FIG. 26

| P(CALCIFICATION ARRANGEMENT) | | | | | CALCIFICATION STATE |
|---|---|---|---|---|---|
| SCATTERED | CLUSTERED | SCATTERED & CLUSTERED | SINGLE | NA | |
| 78/281 | 109/281 | 66/281 | 30/281 | 0 | MALIGNANT |
| 203/514 | 130/514 | 139/514 | 42/514 | 0 | BENIGN |
| 0.0 | 0.0 | 0.0 | 0.0 | 1.0 | NONE |

FIG. 27

| P(PAIN) | | BREAST CANCER STATE |
|---|---|---|
| PRESENT | ABSENT | |
| 3/65 | 62/65 | PRESENT |
| 9/379 | 370/379 | ABSENT |

FIG. 28

| P(NIPPLE DISCHARGE) | | BREAST CANCER STATE |
|---|---|---|
| PRESENT | ABSENT | |
| 1/65 | 64/65 | PRESENT |
| 3/379 | 376/379 | ABSENT |

FIG. 29

| P(PALPABLE MASS) | | | MASS STATE |
|---|---|---|---|
| PRESENT | ABSENT | NA | |
| 0.62 | 0.38 | 0.0 | MALIGNANT |
| 0.43 | 0.57 | 0.0 | BENIGN |
| 0.0 | 0.0 | 1.0 | NONE |

FIG. 30

| FIELD POSITION | FIELD NAME | DEFAULT VALUE | RANGE OF VALUES | CORRESPONDING NODE NUMBER |
|---|---|---|---|---|
| 0 | AGE | 0 | 0-12 | 0 |
| 1 | AGE OF MENARCHE | 0 | 0-3 | 1 |
| 2 | AGE OF FIRST LIFE BIRTH | 0 | 0-4 | 2 |
| 3 | NUMBER OF RELATIVES | 0 | 0-3 | 3 |
| 4 | BREAST CANCER | | | 4 |
| 5 | MASS | | | 5 |
| 6 | CALCIFICATION | | | 6 |
| 7 | ASYMMETRY | 0 | 0-2 | 7 |
| 8 | DEVELOPING DENSITY | 0 | 0-2 | 8 |
| 9 | DILATED DUCT | 0 | 0-2 | 9 |
| 10 | PAIN | 0 | 0-2 | 10 |
| 11 | NIPPLE DISCHARGE | 0 | 0-2 | 11 |
| 12 | ARCHITECTURAL DISTORTION | 0 | 0-2 | 12 |
| 13 | PREVIOUS BIOPSY | 0 | 0-2 | 13 |
| 14 | TUMOR LOCATION | 0 | 0-6 | 14 |
| 15 | MASS MARGIN | 0 | 0-4 | 15 |
| 16 | MASS DENSITY | 0 | 0-3 | 16 |
| 17 | HALO SIGN | 0 | 0-3 | 17 |
| 18 | MASS SIZE | 0 | 0-7 | 18 |
| 19 | PALPABLE MASS | 0 | 0-2 | 19 |
| 20 | CALCIFICATION SHAPE | 0 | 0-5 | 20 |
| 21 | NUMBER OF CALCIFICATIONS IN CLUSTER | 0 | 0-7 | 21 |
| 22 | CALCIFICATION CLUSTER SHAPE | 0 | 0-5 | 22 |
| 23 | CALCIFICATION DENSITY | 0 | 0-5 | 23 |
| 24 | CALCIFICATION SIZE | 0 | 0-6 | 24 |
| 25 | CALCIFICATION ARRANGEMENT | 0 | 0-5 | 25 |

METHOD OF DIAGNOSING BREAST CANCER

CROSS-REFERENCE TO RELATED APPLICATION

This application is a non-provisional which claims priority to provisional application Ser. No. 60/034,383 filed Dec. 27, 1996.

BACKGROUND OF THE INVENTION a. Field of the Invention

The instant invention is directed toward a method of diagnosing breast cancer. More specifically, it relates to a computer-aided diagnosis support tool employing an inference system.

b. Background Art

A woman has a 1 in 8 chance of developing breast cancer in her lifetime. In 1995, an estimated 183,400 women in the United States were newly diagnosed with breast cancer, and 46,240 died of the disease. Screening mammography effectively detects early breast cancers and can increase the likelihood of cure and long-term survival. Differentiating between benign and malignant mammographic findings, however, is difficult, with approximately 75% of mammograms classified "indeterminate."

Successful diagnosis depends on the ability of a physician to detect mammographic abnormalities and to integrate clinical information such as risk factors and physical findings to determine the likelihood of breast cancer. Only 15%–30% of biopsies performed on nonpalpable but mammographically suspicious lesions prove malignant. Unnecessary biopsies are costly in terms of physical and emotional discomfort to the patient. Subsequent radiographic abnormalities from biopsies can be mistaken for cancer. Thus, the cost of screening mammography is increased.

Computer technology in the form of a clinical decision-support tool can be employed to improve the diagnostic accuracy and cost-effectiveness of screening mammography. Automated classification of mammographic findings using discriminant analysis and artificial neural networks (ANNs) has already indicated the potential usefulness of computer-aided diagnosis. ANNs learn directly from observations with a knowledge base of impenetrable numerical connection values. Although they perform well, ANNs do not provide for meaningful explanation generation.

Bayesian networks—also called belief networks or causal probabilistic networks—use probability theory as an underpinning for reasoning under uncertainty. One could use Bayesian networks as the formalism to construct a decision support tool. This tool integrated with a clinical database would provide accurate, reliable, and consistent diagnoses. A Bayesian network could perform a differential diagnosis by specifying the observed symptoms and computing the posterior probability of the various diagnoses using standard probability formulas. The tool would also be able to generate explanations of its reasoning for the physicians who use it. The ability of Bayesian networks to explain their reasoning is an important advantage over ANNs. Physicians generally will not accept and act on a computer system's advice without knowing the basis for the system's decision.

Bayesian Networks provide a number of powerful capabilities for representing uncertain knowledge. Their flexible representation allows one to specify dependence and independence of variables in a natural way through a network topology. Because dependencies are expressed qualitatively as links between nodes, one can structure the domain knowledge qualitatively before any numeric probabilities need be assigned. The graphical representation also makes explicit the structure of the domain model: a link indicates a causal relation or known association. The encoding of independencies in the network topology admits the design of efficient procedures for performing computations over the network. A further advantage of the graphical representation is the perspicuity of the resulting domain model. Finally, since Bayesian networks represent uncertainty using standard probability, one can collect the necessary data for the domain model by drawing directly on published statistical studies.

A Bayesian belief network—a graphical representation of probabilistic information—is a directed acyclic graph. The graph is "directed" in that the links between nodes have directionality, that is, they are "one way." The graph is "acyclic" in that it cannot contain cycles or "feedback" loops. The nodes of the network represent random variables (stochastic)—uncertain quantities—which take on two or more possible values or states. The states of a node define the set of possible values a node can be in at any one time. Each state is associated with a probability value; for each node, these probability values sum to 1. The states for any node are mutually exclusive and completely exhaustive. The directed links signify the existence of direct causal influences or class-property relationships between the connected nodes. The strengths of these nodes are quantified by conditional probabilities. In this formalism, variables are given numerical probability values signifying the degree of belief accorded them, and the values are combined and manipulated according to the rules of standard probability theory.

A Bayesian network contains two types of nodes: nodes with parents and nodes without. A node with at least one parent is represented graphically with a directed link connecting the parent node to the child node. In Bayesian terminology the parent node influences the child node. A node with a set of parents is conditioned on that parent set. A node with no parents is represented graphically with no directed links coming into the node. This latter type of node represents a prior probability assessment and is represented or quantified by an unconditioned prior probability representing prior knowledge.

The strengths of influences between the nodes are represented with conditional-probability matrices associated with the connecting links. For example, if node Z has two parent nodes X and Y, the conditional probability matrix specifies the probabilities of the possible values that Z can assume given all possible combinations of values that X and Y can assume.

The prior and conditional probability values used to build a Bayesian network can be derived directly from published values of sensitivity and specificity and collected from expert opinion.

The primary operation of a Bayesian network is the computation of posterior probabilities. A posterior probability of a variable is the probability distribution for this variable given all its conditioning variables. This inference operation consists of specifying values for observed variables, e.g., setting a node state to one, and computing the posterior probabilities of the remaining variables. The mathematics used in a Bayesian network is described as follows:

Let X be a random variable with n possible states, $x_1, \ldots, x_n$. Let Y be a random variable with m possible states, $y_1, \ldots, y_m$. The probability of a variable X, P(X), is a real number in the interval 0 to 1. P(X)=1 if and only if the event X is certain.

The probability of any event X being in state $x_i$ is denoted by $P(X=x_i)=p$, where p is the degree of belief accorded to X being in state $x_i$.

The conditional probability of any event X being in state $x_i$ given a context Y is denoted by $P(X=x_i|Y)=p$, where p is the degree of belief accorded to X given the context Y.

The joint probability of any events X being in state $x_i$ and Y being in state $y_j$ is denoted by $P(X=x_i, Y=y_j)=p$, where p is the degree of belief accorded to $X=x_i$ and $Y=y_j$.

The probability distribution of a node X with possible states $x_1, x_2, \ldots, x_n$, is denoted by $P(X)=(x_1, x_2, \ldots, x_n)$, given $x_i \geq 0$ and $\Sigma x_i=1$, where $x_i$ is the probability of X being in state $x_i$.

The product rule in probability is denoted by $$P(X|Y) \cdot P(Y) = P(X,Y). \quad [1]$$

The probability distribution of X can be calculated from the joint probability distribution, P(X,Y), by summing over the partitions as denoted by $$P(X) = \sum_{j=1}^{m} P(X, Y). \quad [2]$$

The inversion formula (Bayes Theorem) in probability is denoted by $P(Y|X=e)=P(X=e|Y) \cdot P(Y)/P(X=e)$, where e is user-observed evidence. [3]

A conditional probability distribution is all combinations of the variable X conditioned on its conditioning variable Y. The distribution will contain (number of possible states in X)·(number of possible states in Y) entries. For example, if X is a node with two possible states $x_1, x_2$ and Y is a node with three possible states $y_1, y_2, y_3$, then P(X|Y) is the conditional probability table (vector) of size 2·3=6 containing the real numbers $P(x_i|y_j)$ denoted as shown in FIG. 1. For each state $y_j$ of Y, where i=1, ..., n and j=1 ..., m $$\sum_{i=1,\ldots,n} p(x_i|y_j) = 1.$$

A joint probability distribution is all combinations of the variable X and the variable Y. The distribution will contain (number of possible states in X)·(number of possible states in Y) entries. The joint probability P(X,Y) is calculated using the product rule P(X|Y)·P(Y)=P(X,Y) as shown in FIG. 2. In FIG. 2, each value $p(x_i, y_j)$ is $p(x_i, y_j) \cdot p(y_j)$, for i=1, ..., n and j=1, ..., m The sum of all the joint combinations equals 1.

$$\sum_{i=1,j=1}^{n,m} P(X, Y) = 1$$

SUMMARY OF THE INVENTION

It is desirable to be able to diagnose breast cancer using an inference system that provides a meaningful explanation of its reasoning. The instant invention is a method of diagnosing breast cancer by generating an inference system having a predetermined number of nodes organized into a tree of cliques. After the inference system is initialized, an evidence vector is created and initialized. The evidence vector is then customized or updated by receiving patient-specific evidence. This updated evidence vector is then propagated through the inference system to determine a breast cancer diagnosis. While determine the breast cancer diagnosis, the system can estimate the influence of each piece of patient-specific evidence on the diagnosis. Thus, the system is capable of not only determining and reporting a breast cancer diagnosis based upon patient-specific evidence, but also determining and reporting the estimated influence of each piece of patient-specific evidence considered.

It is an object of the disclosed invention to provide an improved method of diagnosing breast cancer.

A more detailed explanation of the invention is provided in the following description and claims, and is illustrated in the accompanying figures.

BRIEF DESCRIPTION OF THE DRAWINGS

FIG. 1 is a conditional probability, P(X|Y), vector;

FIG. 2 is a joint probability, P(X, Y), vector;

FIG. 4 is the definitions of network's nodes and their possible states;

FIGS. 5A–5J is the demographic risk factor, conditional probability of breast cancer given age, age of menarche, age of first birth, and number of relatives with a history of breast cancer;

FIG. 6 is the demographic risk factor, prior probability for age;

FIG. 7 is the demographic risk factor, prior probability for age of menarche;

FIG. 8 is the demographic risk factor, prior probability for age of first birth;

FIG. 9 is the demographic risk factor, prior probability for number of relatives with a history of breast cancer;

FIG. 10 is the demographic risk factor, prior probability for previous biopsy at same site;

FIG. 11 is an indirect mammographic indication, conditional probability of architectural distortion given breast cancer and previous biopsy at same site;

FIG. 12 is an indirect mammographic indication, conditional probability of asymmetry given breast cancer;

FIG. 13 an indirect mammographic indication, conditional probability of developing density given breast cancer;

FIG. 14 is an indirect mammographic indication, conditional probability of dilated duct given breast cancer;

FIG. 15 is a direct mammographic indication, conditional probability of mass given breast cancer;

FIG. 16 is a direct mammographic indication, conditional probability of calcification given breast cancer;

FIG. 17 is a direct mammographic indication, conditional probability of tumor location given mass;

FIG. 18 is a direct mammographic indication, conditional probability of mass margin given mass;

FIG. 19 is a direct mammographic indication, conditional probability of mass density given mass;

FIG. 20 is a direct mammographic indication, conditional probability of halo sign given mass;

FIG. 21 is a direct mammographic indication, conditional probability of mass size given mass;

FIG. 22 is a direct mammographic indication, conditional probability of calcification shape given calcification;

FIG. 23 is a direct mammographic indication, conditional probability of number in cluster given calcification;

FIG. 24 is a direct mammographic indication, conditional probability of cluster shape given calcifications;

FIG. 25 is a direct mammographic indication, conditional probability of calcification density given calcification;

FIG. 26 is a direct mammographic indication, conditional probability of calcification size given calcification;

FIG. 27 is a direct mammographic indication, conditional probability of calcification arrangement given calcification;

FIG. 28 is a physical indication, conditional probability of pain given breast cancer;

FIG. 29 is a physical indication, conditional probability of nipple discharge given breast cancer;

FIG. 30 is a physical indication, conditional probability of palpable mass given mass;

FIG. 31 depicts the format of an evidence vector;

Figure 32:
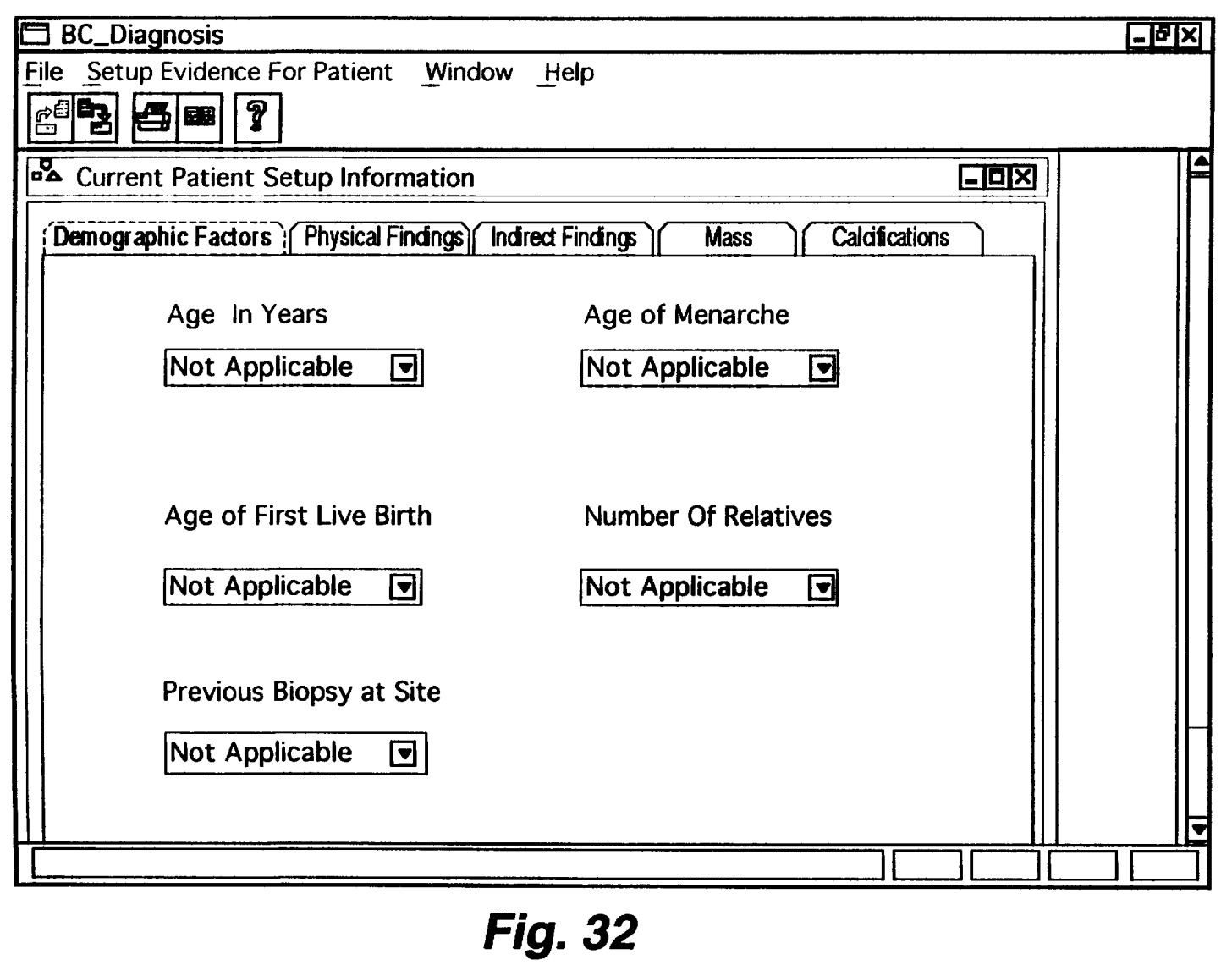

FIG. 32 is a sample data entry screen for demographic factors;

DESCRIPTION OF THE PREFERRED EMBODIMENT

Bayesian networks used in the medical field can express the relationships between diagnoses, physical findings, laboratory test results, and imaging study findings. Physicians can determine the a priori ("pre-test") probability of a disease, and then incorporate laboratory and imaging results to calculate the a posteriori ("post-test") probability. This invention employs a Bayesian network in a decision support tool used in the interpretation of mammograms for the differentiation between benign and malignant lesions of the breast, i.e., detecting breast cancer.

The inference system is logically divided into two components. The first is the knowledge base, and the second is the logic that performs the belief updating when evidence is entered. The invention assumes all the evidence pertains to one particular site identified by mammography. The invention infers the posterior probability of breast cancer at that site based on the available evidence.

System Knowledge Base

Figure 3:
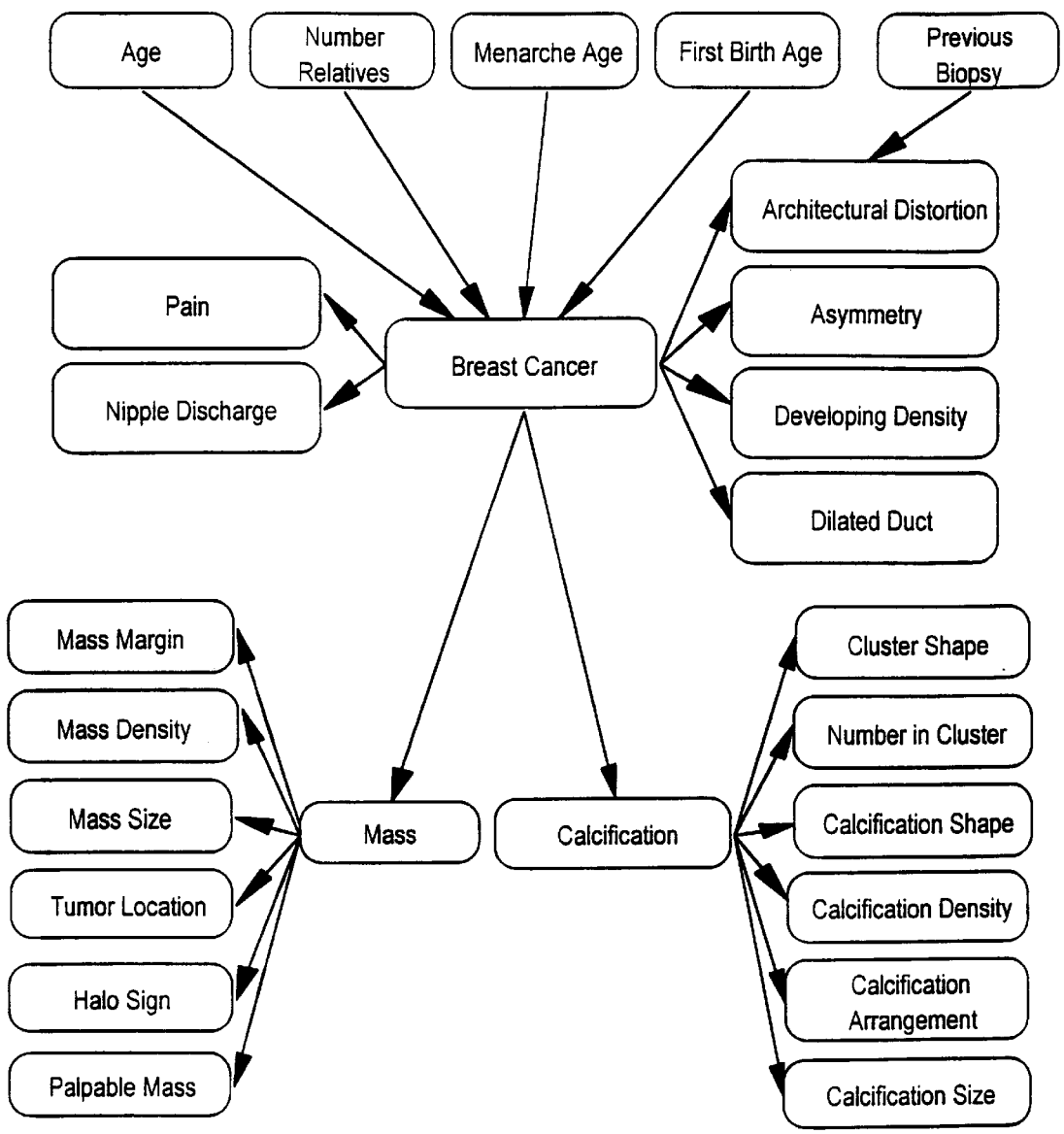
FIG. 3 is a spider chart showing the relationships between the 26 nodes.
Figure 33:
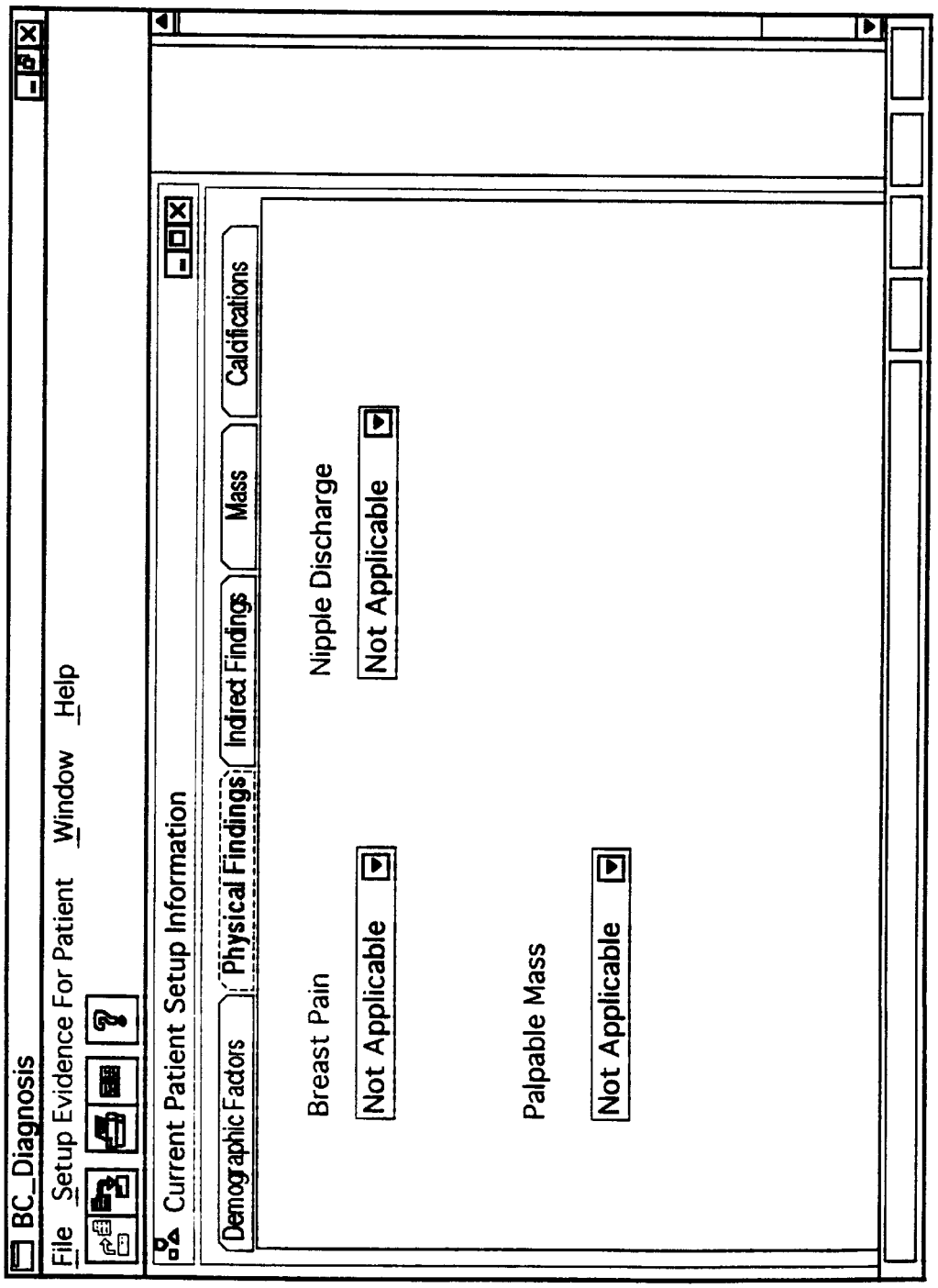
FIG. 33 is a sample data entry screen for physical findings.
Figure 34:
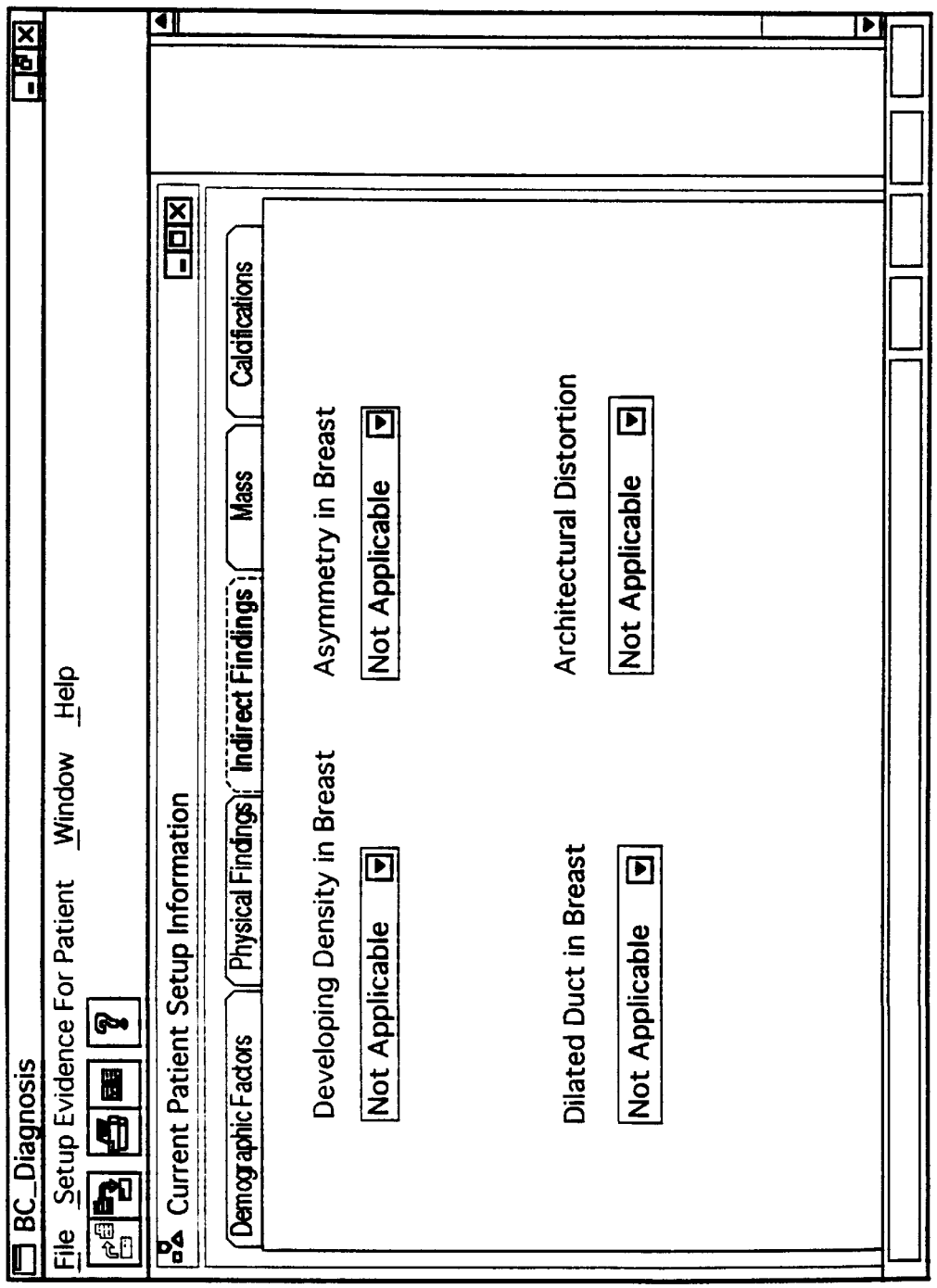
FIG. 34 is a sample data entry screen for indirect mammographic findings.
Figure 35:
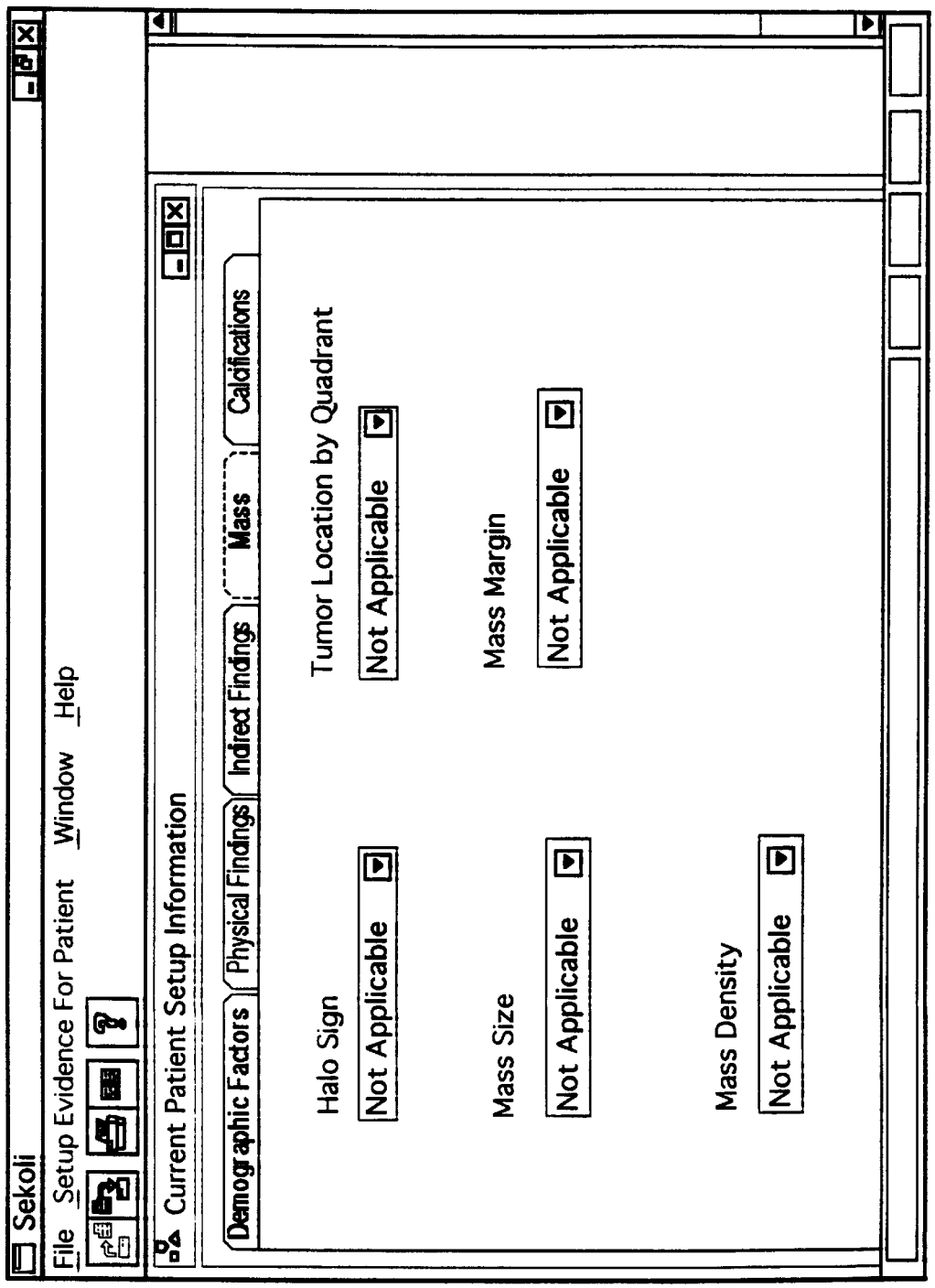
FIG. 35 is a sample data entry screen for direct mammographic mass findings.
Figure 36:
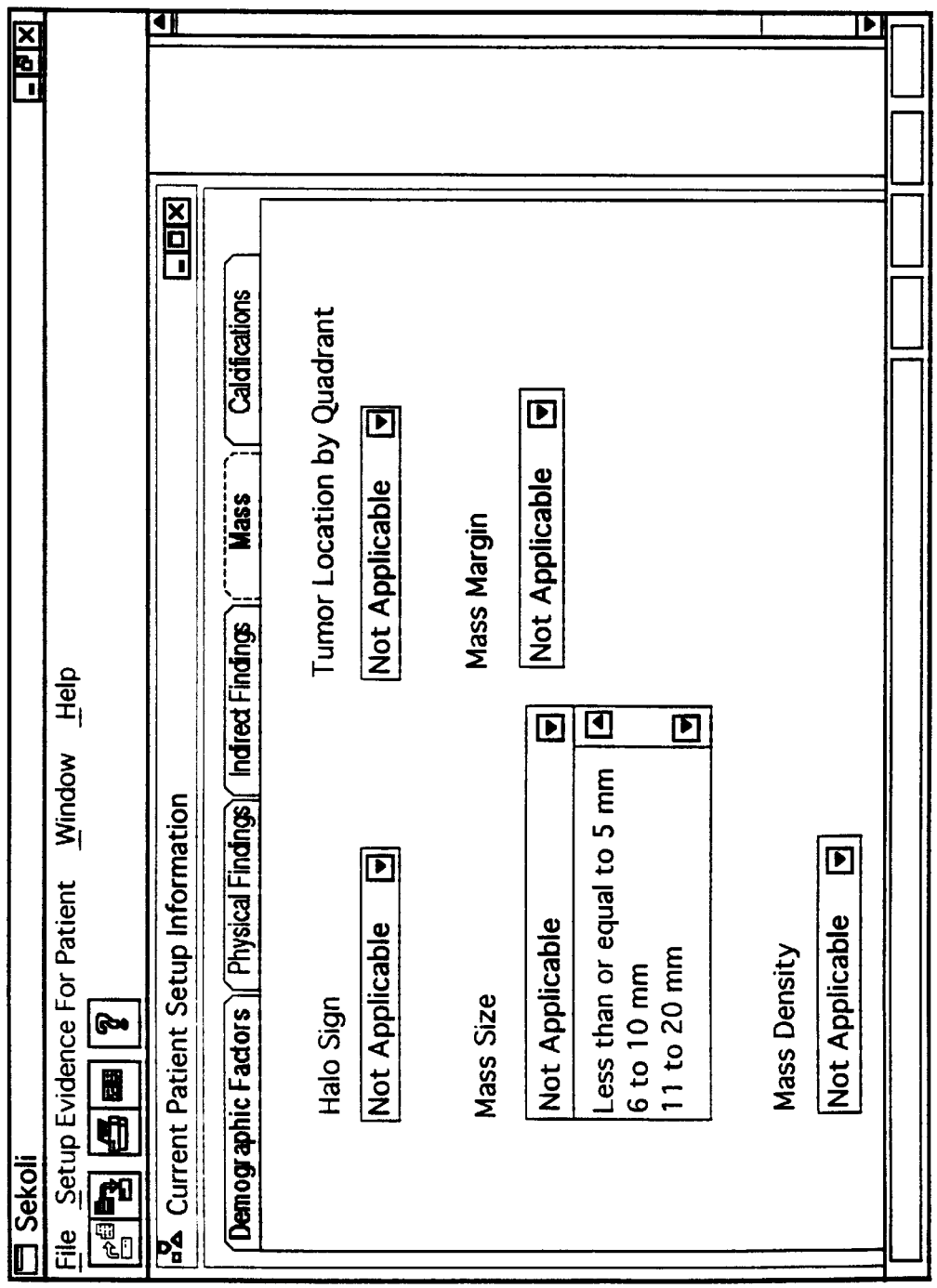
FIG. 36 is a second sample data entry screen for direct mammographic mass findings, shown with the Mass Size drop-down box open.
Figure 37:
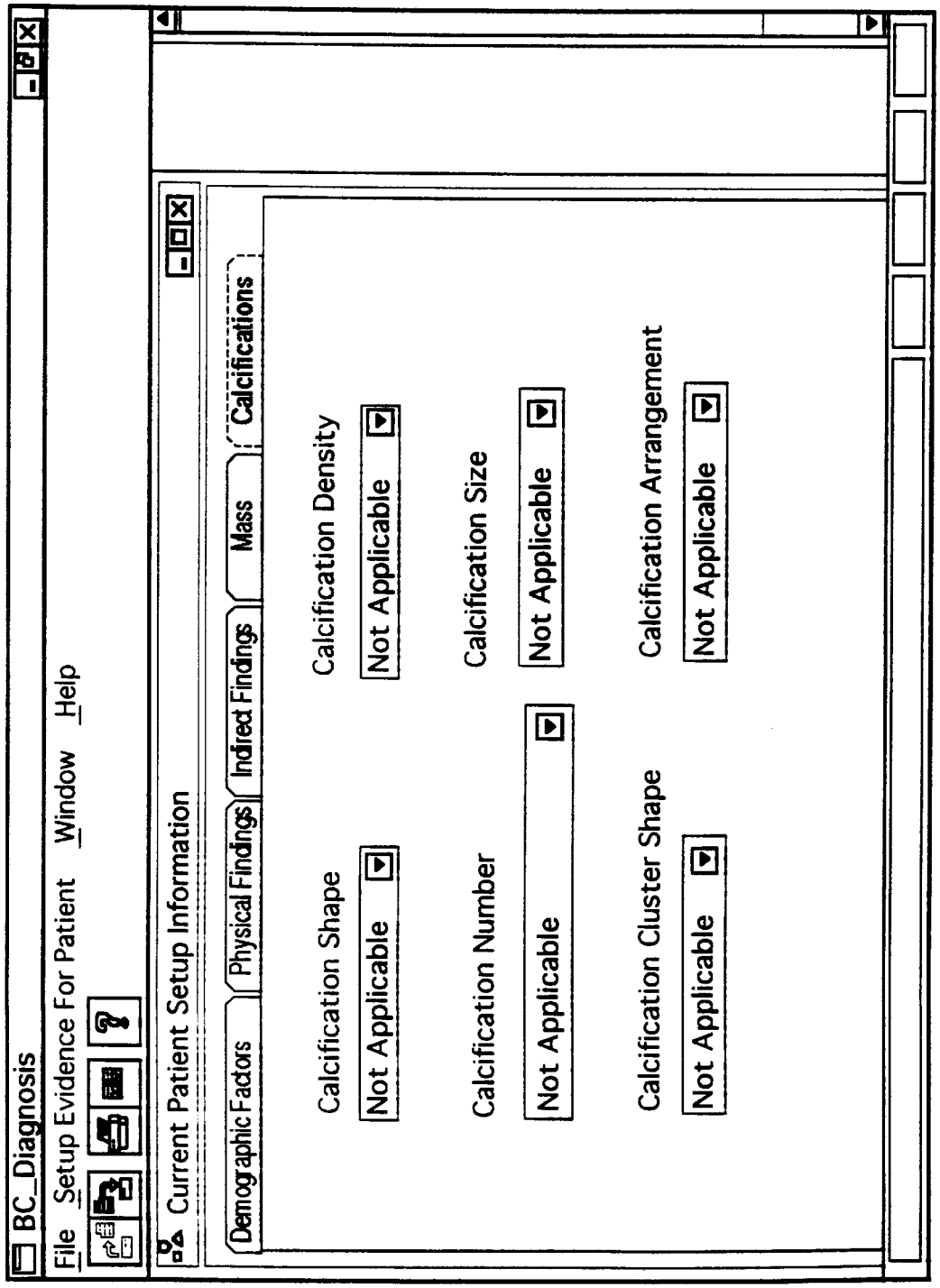
FIG. 37 is a sample data entry screen for direct mammographic calcification findings.

The knowledge base is an encoding of the breast cancer domain in the format of a Bayesian network and contains information used by physicians in diagnosing breast cancer. The topology of the network is presented graphically in FIG. 3. One of the twenty-six nodes of the network is the hypothesis node (i.e., Breast Cancer), which is an inferred node that does not receive direct input from the user. The Mass and Calcification nodes in the center of FIG. 3 are also inferred nodes that do not receive direct input from the user. The remaining twenty-three nodes represent observable evidence. Wherever possible, standardized terminology as proposed in the American College of Radiology's Breast Imaging Reporting and Data Systems lexicon is used.

Breast pain, nipple discharge, and skin thickening are reported by women with breast cancer, but few early-stage cancers are detected by these indicators. The risk factors and physical findings alone are not sufficiently sensitive for malignancy determinations; thus, the use of mammography is an important screening tool.

Benign and malignant masses are differentiated using margin, density, location, size, and the presence of the halo sign. Round, low-density masses with smooth, sharply defined margins are more likely to be benign. Malignant masses are more likely to be high-density, stellate, spiculated, or knobby, with poorly defined margins. Frequently, though, masses are classified as indeterminate, not clearly benign or malignant. Instead of spiculations, many malignant masses display poorly defined or irregular margins.

Calcifications can occur with or without an associated mass. The attributes of size, shape, density, distribution pattern, and number are examined when differentiating between benign and malignant calcifications. Benign calcifications are typically larger (1–4 mm in diameter), coarse, round or oval, and monomorphic (uniform in size and shape). Their distribution pattern is typically scattered or diffuse. If the calcifications are clustered, they number fewer than five per cluster. Some benign calcifications display bizarre, irregular shapes, but because of their large size are considered noncancerous. Malignant calcifications are typically microscopic (<0.5 mm in diameter) and fine, linear branching or rod-shaped, punctate- or stellate-shaped, and pleomorphic (varying in size and shape). In general, the greater the number of calcifications in a cluster, the greater the likelihood of malignancy. As with breast masses, calcifications can display indistinct characteristics making the determination of malignancy difficult. Both benign and malignant calcifications can appear tiny and clustered. Typically, malignant calcifications present with a wide range in size, shape, and density.

Almost 20% of nonpalpable cancers can present with neither mass nor calcification, but with subtle or "indirect" signs of malignancy. Architectural distortion or a developing density (an enlarging area of glandular-tissue density) are strongly indicative of cancer. Dilated mammary ducts and asymmetrical parenchymal density (i.e., greater density in one breast) are less effective indicators. Surgical interventions can confound the diagnosis: a breast biopsy can produce architectural distortion.

The information contained in the knowledge base has been categorized into three primary areas: demographic factors (also referred to as patient-history information), physical examination findings, and mammographic findings extracted by experienced radiologist. Mammographic findings are further subdivided into direct and indirect findings. FIG. 4 presents this categorization and the possible states of each of the twenty-six nodes depicted in FIG. 3. The noninferred portion of the network's knowledge base incorporates five demographic factors (age in years, age of menarche, age of first live birth, number of first order relatives with cancer, previous biopsy at site), three physical examination findings (breast pain, nipple discharge, palpable mass), four indirect mammographic findings (architectural distortion, asymmetry in breast, developing density in breast, dilated duct in breast), and eleven direct mammographic findings (mass margin, mass density, mass size, halo sign, tumor location by quadrant, calcification cluster shape, calcification number, calcification shape, calcification density, calcification arrangement, calcification size).

The prior and conditional probability vectors that quantify the links in the network knowledge base are presented in FIGS. 5A–5J and 6–30. These probabilities were extracted from peer-reviewed medical literature, census data, health statistics reports, and expert opinion.

Initial prior probability values are assigned to the demographic nodes: node 0 (age, FIG. 6); node 1 (menarche age, FIG. 7); node 2 (first birth age, FIG. 8); node 3 (number of relatives, FIG. 9); and node 13 (previous biopsy, FIG. 10). Age statistics were obtained from the National Cancer Institutes and the U.S. Census Bureau, Population Division. Statistics for age of menarche were acquired from the Department of Health, Education, and Welfare, Vital and Health Statistics. Population and Vital Statistics, Statistical Record of Women Worldwide provided statistics for age of first live birth. The number of first order relatives with a known history of breast cancer was estimated based upon information.

Initial conditional probability values are assigned to the remaining nodes: node 4 (breast cancer, FIGS. 5A–5J); node 5 (mass, FIG. 15); node 6 (calcification, FIG. 16); node 7 (asymmetry, FIG. 12); node 8 (developing density, FIG. 13); node 9 (dilated duct, FIG. 14); node 10 (breast pain, FIG. 28); node 11 (nipple discharge, FIG. 29); node 12 (architectural distortion, FIG. 11); node 14 (tumor location, FIG. 17); node 15 (mass margin, FIG. 18); node 16 (mass density, FIG. 19); node 17 (halo sign, FIG. 20); node 18 (mass size, FIG. 21); node 19 (palpable mass, FIG. 30); node 20 (calcification shape, FIG. 22); node 21 (number in cluster, FIG. 23); node 22 (cluster shape, FIG. 24); node 23 (calcification density, FIG. 25); node 24 (calcification size, FIG. 26); and node 25 (calcification arrangement, FIG. 27).

Epidemiologic investigations have reported several risk factors that may increase a woman's chance of developing breast cancer. The incidence of breast cancer increases with age, and is higher after menopause. Early menarche, late childbearing (first live birth after age 30 years or nulliparity), and first order relatives with breast cancer increase the probability of malignancy. The values presented in the table comprising FIGS. 5A–5J, which presents the conditional probability of developing breast cancer considering the risk factors of age, age of menarche, age of first birth, and number of first order relatives with a history of breast cancer, were computed (using data retrieved from the National Cancer Institute's Surveillance Program) by multiplying the relative risk factors by the base risk factors for a specific age group to obtain an adjusted probability.

System Logic

The logic component of the system, which has been programmed using C++, is based on standard probability theory. This software system is a dedicated inference engine that uses Bayesian network theory and techniques to calculate the posterior probability of breast cancer given each case's constellation of observable demographic, physical, and mammographic evidence. The basic calculation formulas used to perform the evidence propagation and belief update of all network nodes are standard probability formulas provided in the background section. The system uses a probability of threshold for breast cancer of 15% (which approximates the positive predictive value of mammographic suspicion) to determine the presence of breast cancer.

The user of this system must input information with respect to predefined demographic factors, physical findings, and mammographic findings. Information for each factor, however, need not be input. The system uses this information to calculate a posterior probability of the presence of breast cancer. The system, additionally, generates an explanatory report describing its reasoning process. The system runs in single record mode, allowing the user to enter information for a single case and process that record immediately, and in batch record mode, allowing the user to enter multiple records and process the batch of records at one time.

The user interface presents a fixed text input form to which the user identifies relevant information. The input format explicitly reflects the structure of the previously described knowledge base. The user interface can be a Microsoft® Windows™-based program requiring the user to enter data using Windows gadgets (see, e.g., FIGS. 32–37), a hypertext document for use on the world wide web, or an input form generated from a commercial database package. The output of an input session is a formatted evidence vector that is translated into probabilistic information for use by the system. An evidence vector is processed one at a time by the system.

The system propagates the evidence through the network and calculates the posterior probability of the hypothesis node, Breast Cancer, given each piece of user-observed evidence. The output from the system is a posterior probability indicating if breast cancer is present, and an English-text explanation of how the evidence vector with its constellation of user-entered evidence influenced the resulting probability.

Figure 38A:
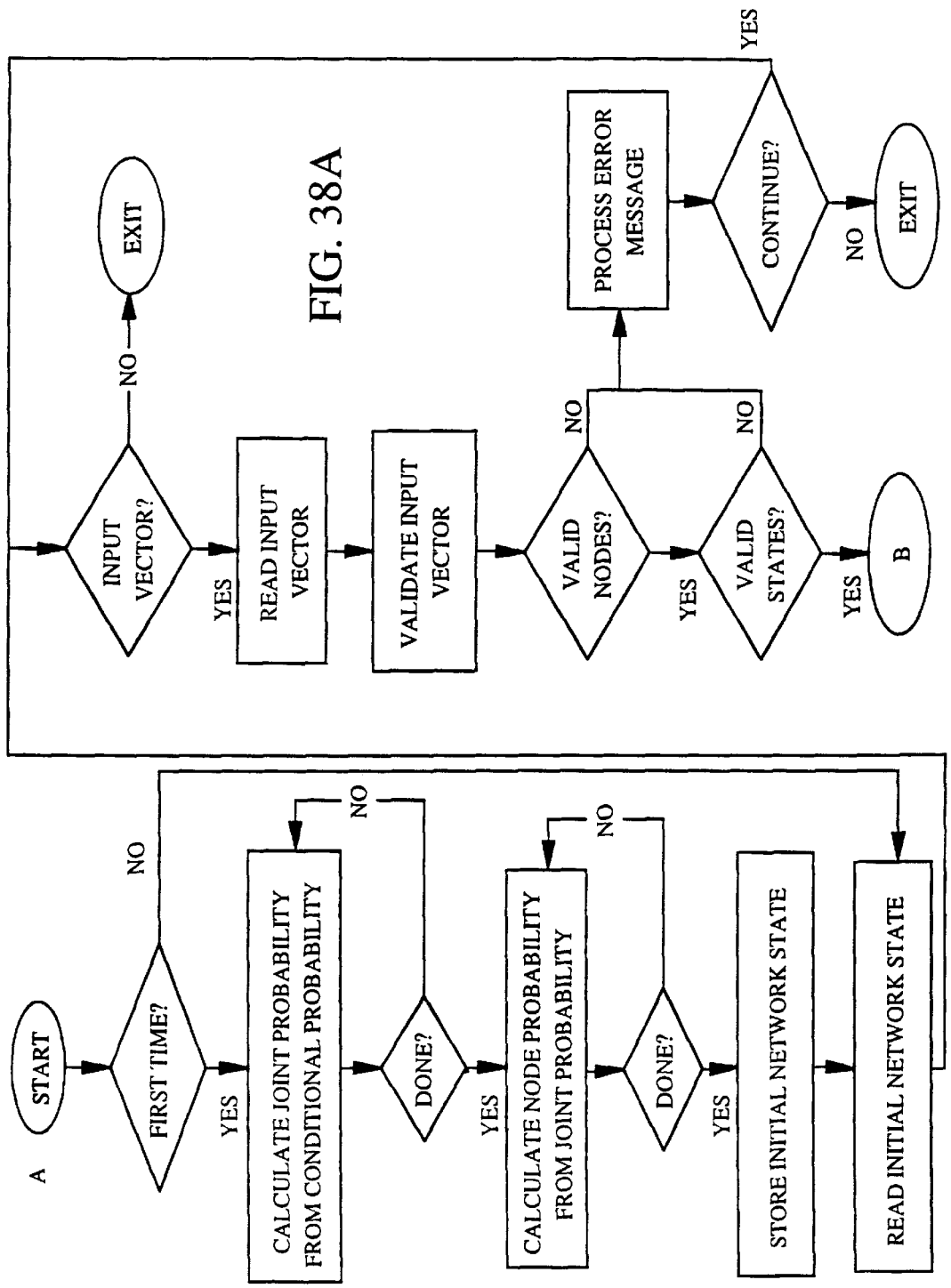
FIGS. 38A and 38B depict the general logic flow of the inference system.
Figure 38B:
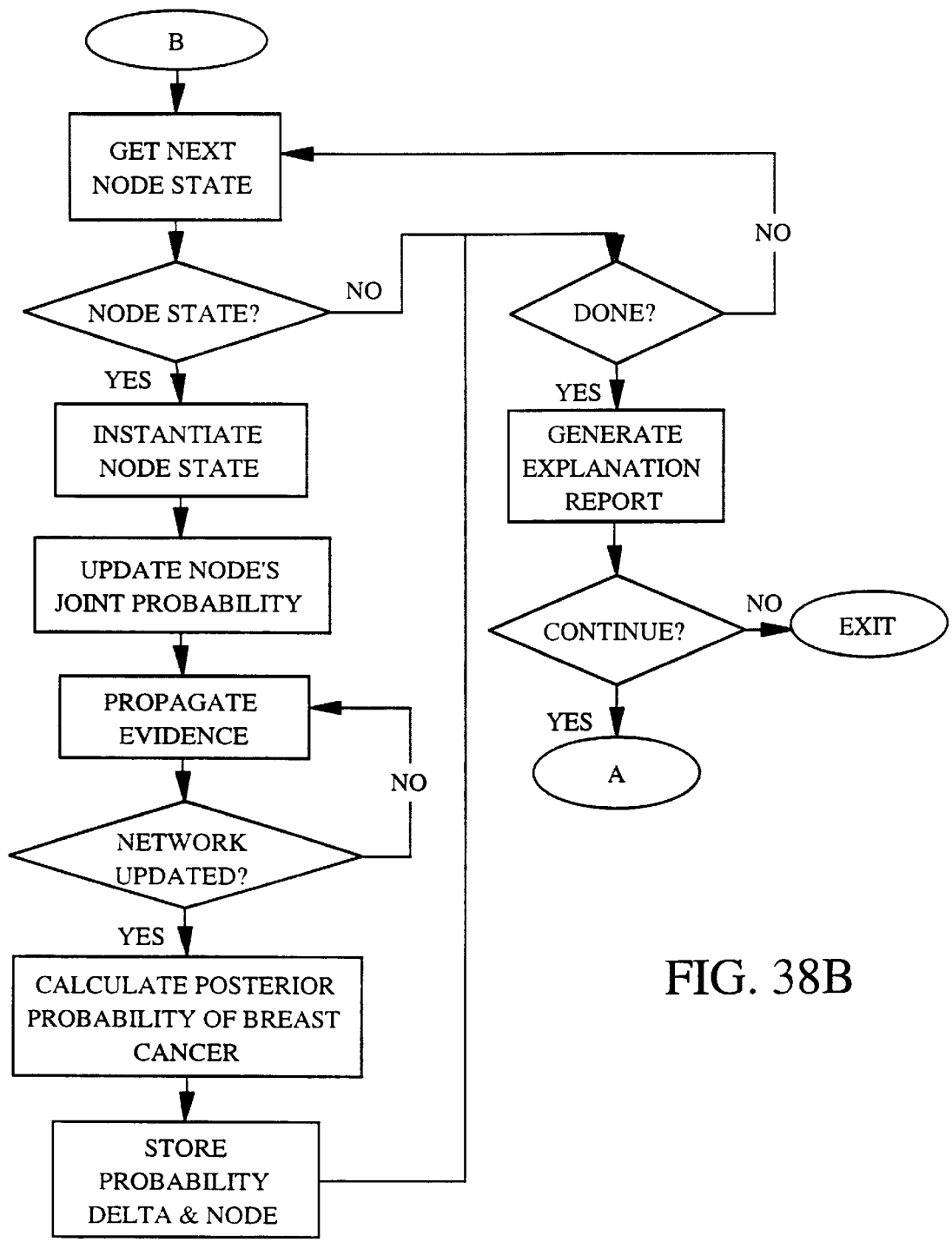

The general logic flow of the inference system is denoted with a flow chart in FIGS. 38A and 38B. If this is initial start up of the system, initial joint probability vectors are calculated and stored for each conditional probability vector. The initial prior and conditional probability vectors used for this calculation are presented in FIGS. 5A–5J and 6–30. The logic that converts the conditional probability distributions to joint probability distributions uses the product rule $P(X|Y, Z) \cdot P(Y) \cdot P(Z) = P(X, Y, Z)$. The conditional and joint distributions are stored internally as one-dimensional vectors (arrays). Each vector entry is a configuration of the variables, and the size (number of vector entries) of a particular vector is a function of the size—the product of the number of possible states—in each variable. For example, if X has n possible states, Y has m possible states, and Z has j possible states, the size of vector $P(X, Y, Z)$ is the product of the number of all possible states for all the concerned variables:

$$n \cdot m \cdot j = nmj.$$

A vector entry contains a configuration (each combination of possible states) of the variables:

$$\{X=x_1, Y=y_1, Z=z_1\} \text{ through } \{X=x_n, Y=y_m, Z=z_j\}.$$

Once all initial joint probability vectors are calculated and stored, the initial prior probabilities (unconditional probability distribution) for each node in the network are calculated and stored. This calculation is done for every node in a joint vector. For two variables X and Y, where X has n possible states and Y has m possible states, the computation for the probability distribution of X is done by summing over all combinations of the conditioned variable Y:

$$P(X = x_i) = \sum_{j=1}^{m} P(X, Y).$$

The prior probability for any variable in a joint vector is computed by conditioning it on all the combinations of the conditioned variables. The prior unconditioned probabilities are stored.

The calculations are done in a predefined sequence such that conditional distributions to be converted to joint distributions, have their prior probability values already calculated:

Calculate joint vector:
p(breast cancer|age, number of relatives, age of menarche, first live birth)·p(age)·p(number of relatives)·p(age of menarche)·p(first live birth)=p(breast cancer, age, number of relatives, age of menarche, first live birth)
Calculate prior probability of breast cancer:
p(breast cancer=present, absent)=Σ(age, number of relatives, age of menarche, first live birth)
Calculate joint vector:
p(pain|breast cancer)·p(breast cancer)=p(pain, breast cancer)
Calculate prior probability of pain:
p(pain=present, absent)=Σp(pain, breast cancer)
Calculate joint vector:
p(nipple discharge|breast cancer)·p(breast cancer)=p(nipple discharge, breast cancer)
Calculate prior probability of nipple discharge:
p(nipple discharge=present, absent)=Σp(nipple discharge, breast cancer)
Calculate joint vector:
p(architectural distortion|breast cancer)·p(breast cancer)=p(architectural distortion, breast cancer)
Calculate prior probability of architectural distortion:
p(architectural distortion=present, absent)=Σp(architectural distortion, breast cancer)
Calculate joint vector:
p(asymmetry|breast cancer)·p(breast cancer)=p(asymmetry, breast cancer)
Calculate prior probability of asymmetry:
p(asymmetry=present, absent)=Σp(asymmetry, breast cancer)
Calculate joint vector:
p(developing density|breast cancer)·p(breast cancer)=p(developing density, breast cancer)
Calculate prior probability of developing density:
p(developing density=present, absent)=Σp(developing density, breast cancer)
Calculate joint vector:
p(dilated duct|breast cancer)·p(breast cancer)=p(dilated duct, breast cancer)
Calculate prior probability of dilated duct:
p(dilated duct=present, absent)=Σp(dilated duct, breast cancer)
Calculate joint vector:
p(mass|breast cancer)·p(breast cancer)=p(mass, breast cancer)
Calculate prior probability of mass:
p(mass=benign, malignant, NA)=Σp(mass, breast cancer)
Calculate joint vector:
p(calcification|breast cancer)·p(breast cancer)=p(calcification, breast cancer)
Calculate prior probability of calcification:
p(calcification=benign, malignant, NA)=Σp(calcification, breast cancer)
Calculate joint vector:
p(mass margin|mass)·p(mass)=p(mass margin, mass)
Calculate prior probability of mass margin:
p(mass margin=spiculated, irregular, relatively well-defined, NA)=Σp(mass margin, mass)
Calculate joint vector:
p(mass density|mass)·p(mass)=p(mass density, mass)
Calculate prior probability of mass density:
p(mass density=low density, high density, NA)=Σp(mass density, mass)
Calculate joint vector
p(mass size|mass)·p(mass)=p(mass size, mass)
Calculate prior probability of mass size:
p(mass size=inSitu, <=5, 6–10, 11–20, >20, multiFocal, NA)=Σp(mass size, mass)
Calculate joint vector:
p(tumor location|mass)·p(mass)=p(tumor location, mass)
Calculate prior probability of tumor location:
p(tumor location=UO, UI, LO, LI, RA, NA)=Σp(tumor location, mass)
Calculate joint vector:
p(halo sign|mass)·p(mass)=p(halo sign, mass)
Calculate prior probability of halo sign:
p(halo sign=present, absent)=Σp(halo sign, mass)
Calculate joint vector:
p(palpable mass|mass)·p(mass)=p(palpable mass, mass)
Calculate prior probability of palpable mass:
p(palpable mass=present, absent)=Σp(palpable mass, mass)
Calculate joint vector:
p(cluster shape|calcification)·p(calcification)=p(cluster shape, calcification)
Calculate prior probability of cluster shape:
p(cluster shape=punctate, round, linear, variable, NA)=Σp(cluster shape, calcification)
Calculate joint vector:
p(number in cluster|calcification)·p(calcification)=p(number in cluster, calcification)
Calculate prior probability of number in cluster:
p(number in cluster=<=5, 6–10, 11–15, 16–25, 26–50, >50, NA)=Σp(number in cluster, calcification)
Calculate joint vector:
p(calcification shape|calcification)·p(calcification)=p(calcification shape, calcification)
Calculate prior probability of calcification shape:
p(calcification shape=linear branching, irregular, indeterminate, round, NA)=Σp(calcification shape, calcification)
Calculate joint vector:
p(calcification density|calcification)·p(calcification)=p(calcification density, calcification)
Calculate prior probability of calcification density:
p(calcification density=1–2, 1–3, 2–3, 3–4, NA)=Σp(calcification density, calcification)
Calculate joint vector:

p(calcification arrangement|calcification)·p(calcification)=p(calcification arrangement, calcification)

Calculate prior probability of calcification arrangement:

p(calcification arrangement=scattered, clustered, scattered & clustered, single, NA)=Σp(calcification arrangement, calcification)

Calculate joint vector:

p(calcification size|calcification)·p(calcification)=p(calcification size, calcification)

Calculate prior probability of calcification size:

p(calcification size=0.05–0.1, 0.05–2, 0.01–1, 0.01–2, 1–3, NA)=Σp(calcification size, calcification)

Calculate joint vector:

p(previous biopsy|breast cancer, architectural distortion)·p(breast cancer)·p(architectural distortion)=p(previous biopsy, breast cancer, architectural distortion)

Calculate prior probability of previous biopsy:

p(previous biopsy=present, absent)=Σp(previous biopsy, breast cancer, architectural distortion)

I Software Initialization

At program startup, the system enters an initial state. First, the member components—nodes and cliques—of the Bayesian network are created and initialized. Second, the Bayesian network is initialized. Third, the joint probability vectors and initial prior probability vectors are calculated and stored. Fourth, an evidence vector is created and initialized. The system is then in a wait state for user evidence to be entered by the graphical user interface in single-patient mode or multiple-patient mode.

Node Creation

The nodes represent the domain variables of the network. The 26 member nodes of the Bayesian network are created and initialized with the following default information:

- number of possible states
- textual name of node for reports
- node number for identification
- number of parent nodes—nodes that are incoming to the current node
- number of children nodes—nodes that are outgoing from the current node
- the size of the associated joint vector, null if no joint vector is associated with the current node
- children nodes
- parent nodes
- clique the node is a member of
- prior probability vector
- conditional probability vector Node Age is created and defaulted as follows:

| | |
|---|---|
| number of possible states | 12 |
| name | Age |
| node number | 0 |
| number of parent nodes | 0 |
| number of children nodes | 1 |
| joint vector size | 0 |
| child node | Breast Cancer |
| parent nodes | none |

| | |
|---|---|
| clique | 0 |
| prior probability vector | FIG. 6 |
| conditional probability vector | none |

Node Age of Menarche is created and defaulted as such:

| | |
|---|---|
| number of possible states | 3 |
| name | Menarche |
| node number | 1 |
| number of parent nodes | 0 |
| number of children nodes | 1 |
| joint vector size | 0 |
| child node | Breast Cancer |
| parent nodes | none |
| clique | 0 |
| prior probability vector | FIG. 7 |
| conditional probability vector | none |

Node Age of First Birth is created and defaulted as follows:

| | |
|---|---|
| number of possible states | 4 |
| name | Birth |
| node number | 2 |
| number of parent nodes | 0 |
| number of children nodes | 1 |
| joint vector size | 0 |
| child node | Breast Cancer |
| parent nodes | none |
| clique | 0 |
| prior probability vector | FIG. 8 |
| conditional probability vector | none |

Node Number of Relatives is created and defaulted as follows:

| | |
|---|---|
| number of possible states | 3 |
| name | Relatives |
| node number | 3 |
| number of parent nodes | 0 |
| number of children nodes | 1 |
| joint vector size | 0 |
| child node | Breast Cancer |
| parent nodes | none |
| clique | 0 |
| prior probability vector | FIG. 9 |
| conditional probability vector | none |

Node Breast Cancer is created and defaulted as follows:

| | |
|---|---|
| number of possible states | 2 |
| name | Breast Cancer |
| node number | 4 |
| number of parent nodes | 4 |
| joint vector size | 864 |
| children nodes | Mass, Calcification, Asymmetry, Developing Density, Dilated Duct, Pain, Nipple Discharge, Architectural Distortion |
| parent nodes | Age, Menarche, Birth, Relatives |
| clique | 0 |
| prior probability vector | calculated by software |
| conditional probability vector | FIGS. 5A–5J |

Node Mass is created and defaulted as follows:

| | |
|---|---|
| number of possible states | 3 |
| name | Mass |
| node number | 5 |
| number of parent nodes | 1 |
| number of children nodes | 6 |
| joint vector size | 6 |
| children nodes | Tumor Location, Mass Margin, Mass Density, Halo Sign, Mass Size, Palpable Mass |
| parent node | Breast Cancer |
| clique | 1 |
| prior probability vector | calculated by software |
| conditional probability vector | FIG. 15 |

Node Calcification is created and defaulted as follows:

| | |
|---|---|
| number of possible states | 3 |
| name | Calcification |
| node number | 6 |
| number of parent nodes | 1 |
| number of children nodes | 6 |
| joint vector size | 6 |
| children nodes | Calc Shape, Calc Number, Calc Cluster Shape, Calc Density, Calc Size, Calc Arrangement |
| parent node | Breast Cancer |
| clique | 2 |
| prior probability vector | calculated by software |
| conditional probability vector | FIG. 16 |

Node Asymmetry is created and defaulted as follows:

| | |
|---|---|
| number of possible states | 2 |
| name | Asymmetry |
| node number | 7 |
| number of parent nodes | 1 |
| number of children nodes | 0 |
| joint vector size | 4 |
| children nodes | none |
| parent ndde | Breast Cancer |
| clique | 3 |
| prior probability vector | calculated by software |
| conditional probability vector | FIG. 12 |

Node Developing Density is created and defaulted as follows:

| | |
|---|---|
| number of possible states | 2 |
| name | Developing Density |
| node number | 8 |
| number of parent nodes | 1 |
| number of children nodes | 0 |
| joint vector size | 4 |
| children nodes | none |
| parent node | Breast Cancer |
| clique | 4 |
| prior probability vector | calculated by software |
| conditional probability vector | FIG. 13 |

Node Dilated Duct is created and defaulted as follows:

| | |
|---|---|
| number of possible states | 2 |
| name | Dilated Duct |

-continued

| | |
|---|---|
| node number | 9 |
| number of parent nodes | 1 |
| number of children nodes | 0 |
| joint vector size | 4 |
| children nodes | none |
| parent nodes | Breast Cancer |
| clique | 5 |
| prior probability vector | calculated by software |
| conditional probability vector | FIG. 14 |

Node Pain is created and defaulted as follows:

| | |
|---|---|
| number of possible states | 2 |
| name | Pain |
| node number | 10 |
| number of parent nodes | 1 |
| number of children nodes | 0 |
| joint vector size | 4 |
| children nodes | none |
| parent nodes | Breast Cancer |
| clique | 6 |
| prior probability vector | calculated by software |
| conditional probability vector | FIG. 28 |

Node Nipple Discharge is created and defaulted as follows:

| | |
|---|---|
| number of possible states | 2 |
| name | Nipple Discharge |
| node number | 11 |
| number of parent nodes | 1 |
| number of children nodes | 0 |
| joint vector size | 4 |
| children nodes | none |
| parent nodes | Breast Cancer |
| clique | 7 |
| prior probability vector | calculated by software |
| conditional probability vector | FIG. 29 |

Node Architectural Distortion is created and defaulted as follows:

| | |
|---|---|
| number of possible states | 2 |
| name | Architectural Distortion |
| node number | 12 |
| number of parent nodes | 2 |
| number of children nodes | 0 |
| joint vector size | 8 |
| children nodes | none |
| parent nodes | Breast Cancer, Previous Biopsy |
| clique | 8 |
| prior probability vector | calculated by software |
| conditional probability vector | FIG. 11 |

Node Previous Biopsy is created and defaulted as follows:

| | |
|---|---|
| number of possible states | 2 |
| name | Previous Biopsy |
| node number | 13 |
| number of parent nodes | 0 |
| number of children nodes | 1 |
| joint vector size | 0 |
| child node | Architectural Distortion |
| parent nodes | none |
| clique | 8 |

Node Tumor Location is created and defaulted as follows:

| | |
|---|---|
| number of possible states | 6 |
| name | Tumor Location |
| node number | 14 |
| number of parent nodes | 1 |
| number of children nodes | 0 |
| joint vector size | 18 |
| children nodes | none |
| parent nodes | Mass |
| clique | 9 |
| prior probability vector | calculated by software |
| conditional probability vector | FIG. 17 |

Node Mass Margin is created and defaulted as follows:

| | |
|---|---|
| number of possible states | 4 |
| name | Mass Margin |
| node number | 15 |
| number of parent nodes | 1 |
| number of children nodes | 0 |
| joint vector size | 12 |
| children nodes | none |
| parent nodes | Mass |
| clique | 10 |
| prior probability vector | calculated by software |
| conditional probability vector | FIG. 18 |

Node Mass Density is created and defaulted as follows:

| | |
|---|---|
| number of possible states | 3 |
| name | Mass Density |
| node number | 16 |
| number of parent nodes | 1 |
| number of children nodes | 0 |
| joint vector size | 9 |
| children nodes | none |
| parent nodes | Mass |
| clique | 11 |
| prior probability vector | calculated by software |
| conditional probability vector | FIG. 19 |

Node Halo Sign is created and defaulted as follows:

| | |
|---|---|
| number of possible states | 3 |
| name | Halo Sign |
| node number | 17 |
| number of parent nodes | 1 |
| number of children nodes | 0 |
| joint vector size | 9 |
| children nodes | none |
| parent nodes | Mass |
| clique | 12 |
| prior probability vector | calculated by software |
| conditional probability vector | FIG. 20 |

Node Mass Size is created and defaulted as follows:

| | |
|---|---|
| number of possible states | 7 |
| name | Mass Size |
| node number | 18 |
| number of parent nodes | 1 |
| number of children nodes | 0 |
| joint vector size | 21 |
| children nodes | none |
| parent nodes | Mass |
| clique | 13 |
| prior probability vector | calculated by software |
| conditional probability vector | FIG. 21 |

Node Palpable Mass is created and defaulted as follows:

| | |
|---|---|
| number of possible states | 2 |
| name | Palpable Mass |
| node number | 19 |
| number of parent nodes | 1 |
| number of children nodes | 0 |
| joint vector size | 6 |
| children nodes | none |
| parent nodes | Mass |
| clique | 14 |
| prior probability vector | calculated by software |
| conditional probability vector | FIG. 30 |

Node Calcification Shape is created and defaulted as follows:

| | |
|---|---|
| number of possible states | 5 |
| name | Calcification Shape |
| node number | 20 |
| number of parent nodes | 1 |
| number of children nodes | 0 |
| joint vector size | 15 |
| children nodes | none |
| parent nodes | Calcification |
| clique | 15 |
| prior probability vector | calculated by software |
| conditional probability vector | FIG. 22 |

Node Calcification Number is created and defaulted as follows:

| | |
|---|---|
| number of possible states | 7 |
| name | Calcification Number |
| node number | 21 |
| number of parent nodes | 1 |
| number of children nodes | 0 |
| joint vector size | 21 |
| children nodes | none |
| parent nodes | Calcification |
| clique | 16 |
| prior probability vector | calculated by software |
| conditional probability vector | FIG. 23 |

Node Calcification Cluster shape is created and defaulted as follows:

| | |
|---|---|
| number of possible states | 5 |
| name | Calcification Cluster Shape |
| node number | 22 |
| number of parent nodes | 1 |

-continued

| | |
|---|---|
| number of children nodes | 0 |
| joint vector size | 15 |
| children nodes | none |
| parent nodes | Calcification |
| clique | 17 |
| prior probability vector | calculated by software |
| conditional probability vector | FIG. 24 |

Node Calcification Density is created and defaulted as follows:

| | |
|---|---|
| number of possible states | 5 |
| name | Calcification Density |
| node number | 23 |
| number of parent nodes | 1 |
| number of children nodes | 0 |
| joint vector size | 15 |
| children nodes | none |
| parent nodes | Calcification |
| clique | 18 |
| prior probability vector | calculated by software |
| conditional probability vector | FIG. 25 |

Node Calcification Size is created and defaulted as follows:

| | |
|---|---|
| number of possible states | 6 |
| name | Calcification Size |
| node number | 24 |
| number of parent nodes | 1 |
| number of children nodes | 0 |
| joint vector size | 18 |
| children nodes | none |
| parent nodes | Calcification |
| clique | 19 |
| prior probability vector | calculated by software |
| conditional probability vector | FIG. 26 |

Node Calcification Arrangement is created and defaulted as follows:

| | |
|---|---|
| number of possible states | 5 |
| name | Calcification Arrangement |
| node number | 25 |
| number of parent nodes | 1 |
| number of children nodes | 0 |
| joint vector size | 15 |
| children nodes | none |
| parent nodes | Calcification |
| clique | 20 |
| prior probability vector | calculated by software |
| conditional probability vector | FIG. 27 |

Cliques Creation

The network, which is a graph of nodes, is converted into a tree of cliques. The 21 cliques of the network correspond to the nodes that comprise the conditional vectors. All cliques are initialized with the following default information:
  number of node members in the clique
  clique number for identification
  root clique indicator
  number of links to other cliques
  list of links to other cliques
  number of common nodes—nodes that a clique has in common with other cliques
  member nodes referenced by node number
  common nodes referenced by node number
  base node Clique 0 is created and defaulted as follows:

| | |
|---|---|
| number of node members | 5 |
| clique number | 0 |
| root clique Boolean | true |
| number of links to cliques | 2 |
| links | null, clique 11 |
| number of common nodes | 1 |
| member nodes | Breast Cancer, Age, Menarche, Birth, Relatives |
| common nodes | Breast Cancer |
| base node | Breast Cancer |

Clique 1 is created and defaulted as follows:

| | |
|---|---|
| number of node members | 2 |
| clique number | 1 |
| root clique Boolean | false |
| number of links to cliques | 12 |
| links | cliques 0, 2, 3, 4, 5, 6, 7, 8, 9, 10, 11, 12 |
| number of common nodes | 2 |
| member nodes | Mass, Breast Cancer |
| common nodes | Breast Cancer, Mass |
| base node | Mass |

Clique 2 is created and defaulted as follows:

| | |
|---|---|
| number of node members | 2 |
| clique number | 2 |
| root clique Boolean | false |
| number of links to cliques | 7 |
| links | cliques 1, 13, 14, 15, 16, 17, 18 |
| number of common nodes | 2 |
| member nodes | Calcification, Breast Cancer |
| common nodes | Breast Cancer, Calcification |
| base node | Calcification |

Clique 3 is created and defaulted as follows:

| | |
|---|---|
| number of node members | 2 |
| clique number | 3 |
| root clique Boolean | false |
| number of links to cliques | 2 |
| links | clique 1, null |
| number of common nodes | 1 |
| member nodes | Asymmetry, Breast Cancer |
| common nodes | Breast Cancer |
| base node | Asymmetry |

Clique 4 is created and defaulted as follows:

| | |
|---|---|
| number of node members | 2 |
| clique number | 4 |
| root clique Boolean | false |
| number of links to cliques | 2 |
| links | clique 1, null |
| number of common nodes | 1 |
| member nodes | Developing Density, Breast Cancer |

-continued

| | |
|---|---|
| common nodes | Breast Cancer |
| base node | Developing Density |

Clique 5 is created and defaulted as follows:

| | |
|---|---|
| number of node members | 2 |
| clique number | 5 |
| root clique Boolean | false |
| number of links to cliques | 2 |
| links | clique 1, null |
| number of common nodes | 1 |
| member nodes | Dilated Duct, Breast Cancer |
| common nodes | Breast Cancer |
| base node | Dilated Duct |

Clique 6 is created and defaulted as follows:

| | |
|---|---|
| number of node members | 2 |
| clique number | 6 |
| root clique Boolean | false |
| number of links to cliques | 2 |
| links | clique 1, null |
| number of common nodes | 1 |
| member nodes | Pain, Breast Cancer |
| common nodes | Breast Cancer |
| base node | Pain |

Clique 7 is created and defaulted as follows:

| | |
|---|---|
| number of node members | 2 |
| clique number | 7 |
| root clique Boolean | false |
| number of links to cliques | 2 |
| links | clique 1, null |
| number of common nodes | 1 |
| member nodes | Nipple Discharge, Breast Cancer |
| common nodes | Breast Cancer |
| base node | Nipple Discharge |

Clique 8 is created and defaulted as follows:

| | |
|---|---|
| number of node members | 3 |
| clique number | 8 |
| root clique Boolean | false |
| number of links to cliques | 2 |
| links | clique 1, null |
| number of common nodes | 1 |
| member nodes | Architectural Distortion, Breast Cancer, Previous Biopsy |
| common nodes | Breast Cancer |
| base node | Architectural Distortion |

Clique 9 is created and defaulted as follows:

| | |
|---|---|
| number of node members | 2 |
| clique number | 9 |
| root clique Boolean | false |
| number of links to cliques | 2 |
| links | clique 1, null |
| number of common nodes | 1 |
| member nodes | Tumor Location, Mass |

-continued

| | |
|---|---|
| common nodes | Mass |
| base node | Tumor Location |

Clique 10 is created and defaulted as follows:

| | |
|---|---|
| number of node members | 2 |
| clique number | 10 |
| root clique Boolean | false |
| number of links to cliques | 2 |
| links | clique 1, null |
| number of common nodes | 1 |
| member nodes | Mass Margin, Mass |
| common nodes | Mass |
| base node | Mass Margin |

Clique 11 is created and defaulted as follows:

| | |
|---|---|
| number of node members | 2 |
| clique number | 11 |
| root clique Boolean | false |
| number of links to cliques | 2 |
| links | clique 1, null |
| number of common nodes | 1 |
| member nodes | Mass Density, Mass |
| common nodes | Mass |
| base node | Mass Density |

Clique 12 is created and defaulted as follows:

| | |
|---|---|
| number of node members | 2 |
| clique number | 12 |
| root clique Boolean | false |
| number of links to cliques | 2 |
| links | clique 1, null |
| number of common nodes | 1 |
| member nodes | Halo Sign, Mass |
| common nodes | Mass |
| base node | Halo Sign |

Clique 13 is created and defaulted as follows:

| | |
|---|---|
| number of node members | 2 |
| clique number | 13 |
| root clique Boolean | false |
| number of links to cliques | 2 |
| links | clique 1, null |
| number of common nodes | 1 |
| member nodes | Mass Size, Mass |
| common nodes | Mass |
| base node | Mass Size |

Clique 14 is created and defaulted as follows:

| | |
|---|---|
| number of node members | 2 |
| clique number | 14 |
| root clique Boolean | false |
| number of links to cliques | 2 |
| links | clique 1, null |
| number of common nodes | 1 |
| member nodes | Palpable Mass, Mass |

-continued

| | |
|---|---|
| common nodes | Mass |
| base node | Palpable Mass |

Clique 15 is created and defaulted as follows:

| | |
|---|---|
| number of node members | 2 |
| clique number | 15 |
| root clique Boolean | false |
| number of links to cliques | 2 |
| links | clique 2, null |
| number of common nodes | 1 |
| member nodes | Calcification Shape, Calcification |
| common nodes | Calcification |
| base node | Calcification Shape |

Clique 16 is created and defaulted as follows:

| | |
|---|---|
| number of node members | 2 |
| clique number | 16 |
| root clique Boolean | false |
| number of links to cliques | 2 |
| links | clique 2, null |
| number of common nodes | 1 |
| member nodes | Calcification Number, Calcification |
| common nodes | Calcification |
| base node | Calcification Number |

Clique 17 is created and defaulted as follows:

| | |
|---|---|
| number of node members | 2 |
| clique number | 17 |
| root clique Boolean | false |
| number of links to cliques | 2 |
| links | clique 2, null |
| number of common nodes | 1 |
| member nodes | Calcification Cluster Shape, Calcification |
| common nodes | Calcification |
| base node | Calcification Cluster Shape |

Clique 18 is created and defaulted as follows:

| | |
|---|---|
| number of node members | 2 |
| clique number | 18 |
| root clique Boolean | false |
| number of links to cliques | 2 |
| links | clique 2, null |
| number of common nodes | 1 |
| member nodes | Calcification Density, Calcification |
| common nodes | Calcification |
| base node | Calcification Density |

Clique 19 is created and defaulted as follows:

| | |
|---|---|
| number of node members | 2 |
| clique number | 19 |
| root clique Boolean | false |
| number of links to cliques | 2 |
| links | clique 2, null |
| number of common nodes | 1 |

-continued

| | |
|---|---|
| member nodes | Calcification Size, Calcification |
| common nodes | Calcification |
| base node | Calcification Size |

Clique 20 is created and defaulted as follows:

| | |
|---|---|
| number of node members | 2 |
| clique number | 20 |
| root clique Boolean | false |
| number of links to cliques | 2 |
| links | clique 2, null |
| number of common nodes | 1 |
| member nodes | Calcification Arrangement, Calcification |
| common nodes | Calcification |
| base node | Calcification Arrangement |

Bayesian Network Initialization

The Bayesian network, BC_Diagnosis, is the structure that embodies the dependencies of the member domain nodes. The Bayesian network structure is created and defaulted with the following information:

| | |
|---|---|
| textual name | BC_Diagnosis |
| number of nodes | 26 |
| number of cliques | 21 |
| hypothesis node | Breast Cancer |
| nodes | nodes 0 through 25 |
| cliques | cliques 0 through 20 |

Joint Probability Vector Initialization

Each clique has a base node that has a joint probability and a conditional probability vector. The joint probability vectors are initialized at system startup. Each node has a prior probability vector. At system startup, the initialized joint vectors are used to calculate the initial prior probability vectors for all nodes. The initial prior probability vectors represent the state of the Bayesian network with no evidence applied.

Calculation of the initial joint vectors is started at the clique marked as the root clique. The remaining cliques are calculated by traversing the clique tree in order of the clique links. At each clique, the joint vector is initialized by vector multiplication of the conditional vector and the prior probability vectors of the conditioning nodes. For the network comprised of n cliques:

```
for any clique C_i, i=0 ... n-1
    where C_i is comprised of member nodes X_j, j=0 ... m-1,
    X_0 is the base node,
    X_1 ... X_{m-1} are the conditioning nodes,
    for all cliques
        initialize joint vector for C_i:
        p(x_0,x_1, ... x_{m-1})=p(x_i | x_1, ... ,x_{m-1}) · p(x_1) ... · p(x_{m-1})
        mark C_i as updated
        if C_i (link) is not NULL,
            if C_i is not marked as updated, continue
end_for
```

Prior Probability Vector Initialization

Each node has a prior probability vector. An initial prior probability vector is calculated during the joint vector initialization calculations as described above. For each node, its initial prior probability vectors is calculated and stored.

Each clique's joint vector is used to calculate its (the clique's) member nodes' prior probability vectors.

```
for any clique C_j, i = 0 . . . n-1
    where C_i is comprised of member nodes X_j, j = 0 . . . m-1,
    X_0 is the base node,
    X_1 . . . X_{m-1} are the conditioning nodes,
    X_i has possible states 0 . . . p-1,
    with joint vector, p( x_0, x1, . . . x_{m-1} )
    for all nodes in C_i, calculate the prior probability vector for node X_j
```

$$P(\overset{p}{\underset{j=0}{X_j}}) = (P(X_0, ..., X_{m-1})X_0, ..., X_{j-1}, X_{J+1}, ... X_{m-1}$$

end_for

Evidence Vector Initialization

The network creates an evidence vector at system initialization. The fields of this evidence vector are shown in FIG. 31. This vector contains an entry for each node in the network. Its entries are initialized to default values, indicating no evidence has been received by the system:

```
for any Evidence_Vector of size n,
    where n is the number of nodes in the network
    for all elements E_i, i=0, ... ,n-1
        Set E_i to Default_Value
end_for
```

Upon receipt of evidence, this vector is modified to contain, for any node that received evidence, the state that is certain. The entry of evidence is discussed further below.

II Evidence Entry and Propagation

Evidence is entered into the network by indicating that a node of the network is in a known state. User-entered evidence can be applied to nodes age in years, age of menarche, age of first life birth, number of first order relatives with breast cancer, previous biopsy at site, breast pain, nipple discharge, palpable mass, architectural distortion, asymmetry in breast, developing density in breast, dilated duct in breast, mass margin, mass density, mass size, halo sign, tumor location by quadrant, calcification cluster shape, calcification number, calcification shape, calcification density, calcification arrangement, and calcification size. As previously stated, nodes breast cancer, mass, and calcification do not accept user evidence.

Evidence Entry

User-observed evidence is input into the inference system by way of an encoded evidence vector containing evidence findings for each particular patient. In the preferred embodiment, these evidence findings are entered into the system through a graphical user interface (GUI). Sample data entry windows of this GUI are presented in FIGS. 32–37. The user selects the specified evidence through the menus of the GUI.

The system is capable of acquiring evidence in single-patient mode or multiple-patient mode. In single-patient mode, evidence is entered for one patient. The system processes this single case when notified by the user that the evidence entry is complete. The single-patient mode is the system default mode. If the user selects multiple-patient mode, evidence is entered for multiple patient during a single session. The system creates a batch file of evidence vectors—creating separate evidence vectors for each patient case—and when notified by the user, processes all the evidence vectors sequentially. In both modes, the system generates separate patient result files.

For single-patient mood, one evidence vector (Evidence_Vector[k]) is created and initialized. For multiple-patient mood, an evidence vector is created for each patient case.

```
for any element E_i of the Evidence_Vector[k],
    where i=0, ... ,n-1, element E_i has m possible states, and k=1, ... , p-1
    set E_i of Evidence_Vector[k] to Evidence_Value(j), where j=0 ... m-1
```

Each evidence vector consists of separated data units or fields. The position of each field corresponds to a numbered node in the network. FIG. 31 presents the format of the evidence vector fields and their relationships to the nodes of the network. The value of each field is an encoding of a possible node state (except for the fields corresponding to the nodes that are incapable of taking on evidence, i.e., nodes 4, 5, and 6, corresponding to breast cancer, mass, and calcification, respectively). The record is preloaded to default values for each field, and user-entered evidence can replace these default values with actual findings. The encoding scheme of each field assigns an integer, starting with zero and incrementing sequentially, to each state of a node. For example, the node "age in years" has twelve possible states, which represent twelve categories of ages. The integer zero is assigned to the default value for this node, 1 is assigned to state 20–24, 2 to state 25–29, and so on.

Each evidence vector is verified to be correct. The vector is checked for correct number of fields and field values within range of the corresponding node. An error message is generated and processing of this vector halts, if the syntax of the vector is invalid. The error message indicates what the error condition is—an invalid state for a particular node or a missing node field. Upon successful validation of an evidence vector, the vector is used to drive the evidence propagation through the network.

Evidence Vector Propagation

When the user notifies the system that evidence acquisition is complete, the system performs the evidence propagation or belief updating of the network in response to that evidence. The user-observed evidence is extracted from the validated evidence vector and used to update the joint and prior probability vectors for each node in the network. A new hypothesis node, Breast Cancer, prior probability vector is also calculated.

The processing order of the evidence is constrained by the evidence vector fields ordering. For example, if the only evidence observed by the user is age (corresponding to field 0) and mass margin (corresponding to field 15), age evidence is processed first and mass margin evidence second. Evidence that is not user-observed contains default values in the evidence vector and will not be processed by the propagation logic. Fields containing user-observed evidence are processed in sequential order, and are in turn propagated through the network. All prior unconditional probability distributions are updated based on the user-observed evidence in the evidence vector.

During an evidence propagation session, the system scans an evidence vector (Evidence_Vector[k]) for all user-entered evidence and processes a single user-entered evidence value at a time. As long as there is another unprocessed node state in the evidence vector, the current node state is extracted and used to create a new prior probability for that node. Because the extracted evidence vector value for the node is the user-observed evidence, the prior unconditional distribution for this node must be updated. The state in the probability distribution which corresponds to the user-observed value is set to one indicating certainty, and the remaining states set to zero indicating an impossible state.

The updated probability distribution is then used to update the joint vectors it is a member of by use of Bayes inversion formula [3]. After the joint vector is updated by the evidence, each member node has its prior unconditional distribution recalculated to reflect the impact of the evidence on it. This is done by summing out the distribution using formula [2]. The new prior unconditional distributions of the members of the joint vector are in turn used to update joint vectors they are neighbors of. Updating of joint vectors and recalculations of prior unconditional distributions of members of updated joint vectors continues until each node in the network is updated exactly one time.

The propagation path is facilitated by storing the network graph in an intermediate structure, which is a tree in which the nodes of the tree represent the joint distributions of the network and the links encode the information concerning which joint distributions are related by common variables. The propagation path is a tree traversal, starting at the node that contains the observed evidence member, and visiting each node exactly one time. The tree traversal walks the tree by checking if a neighbor node has been updated. If not, the neighbor node is updated—Bayes inversion formula [3]— and prior unconditional distributions are calculated— summing over partitions [2]. The new distributions are used in turn to update their neighbors until each node in the tree has been updated. The only node we are interested in is the hypothesis node, Breast Cancer. The prior unconditional probability distribution is extracted from the joint vector in which Breast Cancer is a member.

Once a piece of evidence that the user entered has been propagated through the network, the posterior probability distribution for the hypothesis node, Breast Cancer, is calculated. This is done by computing the prior probability unconditional distribution for breast cancer from its joint distribution and summing over all the combinations of the conditioned variables. The newly calculated posterior distribution is stored as a tuple containing additionally the previous posterior probability and the associated piece of evidence: new posterior probability, old posterior probability, and evidence. As each piece of observed evidence is processed by the system, a tuple is added to create a trace of evidence impact on the hypothesis node. The node that received the evidence is also saved.

For each evidence vector, the system loops through each element ($E_i$) of the vector, checking if the user has entered evidence for the corresponding node. If an element is the default value, the system checks the next element. When an element is detected as having received user-entered evidence, the system initiates the network update process. The network update process traverses the clique tree, starting at the clique ($C_i$) whose member received the user-entered evidence, and continues in order of that clique's clique link list. Upon completing the network updating for a single user-entered evidence value, the system stores the previous and current value of the hypothesis node, Breast Cancer. The network updating continues until all elements of the evidence vector are processed.

```
for an Evidence_Vector[k]
    for each element E_i of the Evidence_Vector[k]
        if element E_i is a valid state for the associated node
            set the node's probability evidence vector to contain
                the value 1 for the certain state, and values 0 for
                the other states
            mark the node as receiving evidence
            call routine BNReceiveEvidence() to update the
                network
            store the unmodified and modified prior probability
                vector of the hypothesis node
            call BNExplainReasoning() to generate and store the
                affect element E_i has on the evidence node
            for all nodes, except the nodes that are marked as
                receiving evidence, clear update flags
            end_for
            increment evidence count for clique evidence node is a
                member of
    end_for
end_for
```

Process Initial Clique (BNReceivedEvidence( ))

As the system scans an evidence vector for an element that has received user-entered evidence, the network updating begins at the clique of a node that received user-entered evidence. The node is marked as receiving evidence, and the node's current prior probability vector is set to the evidence vector. The evidence vector, which represents any node's n possible states, contains 0 for the sates that are impossible and a 1 for the state that the user has selected as known.

```
for the node marked as receiving evidence
    determine its clique C_i
    mark clique C_i as receiving evidence
    store node number at clique C_i
    set the node's current prior probability to the evidence vector
    call BNVisitClique() to begin evidence propagation from C_i
end_for
```

Traverse the Clique Tree (BNVisitClique( ))

A user-entered evidence value is propagated through the network, starting at the clique of the node that received the evidence, and traversing the clique tree in order of the link lists of each clique, $C_i$.

```
for all cliques C_i
    if a clique C_i is valid
        call BNProcessClique() to process all nodes in the clique C_i
        mark clique C_i as updated
    if left link of clique C_i is valid
        if left-linked clique C_i is not marked as updated
            call BNVisitClique() to traverse those links
        for all valid clique C_i right links
            if right-linked clique C_i is not marked updated
                call BNVisitClique() to transverse those links
        end_for
end_for
```

Prepare Clique for Updating (BNProcessClique( ))

During the network update process, a clique $C_i$'s joint vector is updated by the evidence. Once a joint vector has been updated, all its member nodes—except those that have received user-entered evidence—have their prior probability vectors updated.

```
for each clique C_i
    get base node of clique C_i
    get number of common nodes of clique C_i
    get common nodes of clique C_i
    get number of nodes in clique C_i
    propagate evidence starting at clique C_i
    call BNPropagateEvidence(C_i)
end_for
```

Update a Clique (BNPropagateEvidence( ))

A clique $C_i$ is marked as receiving evidence, if one of its member nodes is the node that received user-entered evidence during this propagation session. Clique $C_i$'s joint vector is updated. If clique $C_i$ is marked as receiving evidence, the node that received evidence is used to calculate the new joint vector. This node's evidence vector is multiplied by the clique's joint vector. This product is divided by the node's previous prior probability vector. If clique $C_i$ is not marked as receiving evidence, its joint vector is updated by multiplying it by the clique $C_i$'s common node. This product is divided by the common node's previous prior probability vector. The new joint vector is stored at clique $C_i$. All node members of clique $C_i$, except nodes that have been marked updated, have new current prior probabilities calculated. This is done through a call to routine BNCalcPriorProbs() passing the node number and the clique number. When all nodes in clique $C_i$ are marked as updated, clique $C_i$ is marked as updated.

```
        if all nodes in clique C_i are marked as receiving user evidence,
return
        if this clique C_i is marked as receiving user evidence,
            retrieve node that received evidence
            calculate new joint vector for clique C_i
            for any clique C_i , i=0 ... n-1
                where C_i is comprised of member nodes X_j, j=0 ... m-1,
                X_j has possible states 0 ... p-1, with joint vector, p(x_0, x1,
                ... x_{m-1})
                Pnew(x_0,x_1, ... x_{m-1})=(P(x_0,x_1, ... x_{m-1}) · p(node=
                    evidence) / p(node))
                    where p(node) denotes the prior probability
                    vector of node, where p(node = evidence)
                    denotes the evidence vector of node
        else
            retrieve common node[i]
            calculate new joint vector for clique C_i
            for any clique C_i, i=0 ... n-1
                Pnew(X_0,x_1, ... x_{m-1})=(P(x_0,x_1, ... x_{m-1}) · p(node
                    =common[i]) / p(node))
                    where p(node) denotes the prior
                    probability vector of node, where p(node=
                    common[i]) denotes the evidence vector
                    of node
        or all nodes that are not marked as receiving evidence
            set current prior probability vectors,
            BNCalcPriorProbs()
        end_for
mark clique as updated
```

Update Prior Probability Vectors (BNCaclPriorProbs( ))

During the network update process, after a clique $C_i$'s joint vector is recalculated to account for the user-entered evidence, clique $C_i$'s member nodes have their prior probability vectors updated. Each member node has its previous prior probability vector set to its current prior probability vector. Each member node then has its current prior probability vector recalculated.

```
for a node N_i, in clique C_i,
    if node is marked as receiving user evidence, return
    if node is marked as updated, return
    get number of node members in clique C_i
    get node N_i's clique index
    get base node of clique C_i
    get joint vector of clique C_i
    set node N_i's previous prior probability vector to node N_i's current
        prior probability vector
    calculate new prior probability vector for node N_i in clique C_i
```

$$P(X_j) = \sum_{j=0}^{P} (P(X_0, ..., X_{m-1})X_0, ..., X_{j-1}, X_{J+1}, ... X_{m-1}$$

```
    set node N_i's current prior probability vector to node N_i's newly
        calculated prior probabilty vector
    normalize node N_i's current prior probabilities
    mark node N_i updated
end_for
```

Explain Reasoning (BNExplainReasoning( ))

After all evidence for a specific record has been propagated through the network and the posterior distribution of breast cancer, given all the instantiated evidence, has been calculated, the system constructs an explanatory report. This textual report describes the evidence input, the impact of each piece of evidence on the posterior distribution of breast cancer given current evidence, and the final calculated probability of breast cancer on a case or evidence vector basis. This is a tracking of how each piece of evidence impacted the hypothesis node, Breast Cancer, and provides the user with a trace of the system reasoning.

The logic in this section uses the set of tuples generated during evidence propagation each time the hypothesis node, Breast Cancer, was updated. A numeric comparison is done on each tuple, comparing the old and new posterior probabilities. The delta or difference in the value is used to generate text indicating a percentage change (increase, decrease, or no change) in the new posterior probability given a piece of evidence. A description is generated, including the values of the previous and current prior probability vectors, the node that received evidence, and the evidence state the user entered. After all evidence is propagated, the cumulative affect of the total evidence is calculated, and a description is generated. The results are formatted into a textual report, which, in addition to the textual explanations, also contains time stamping and case identification information. The report is archived electronically and is available for hard copy printout. A typical output file contains the following information:

```
Breast Cancer Diagnosis
Patient: Jane Doe
Date: December 10, 1997
File Number: nnn
Doctor/Clinic: Marcus Welby, M.D.
Evidence entered for patient Jane Doe is:
    Patient History
        Age: 45
        Age menstruation started: 13
        No children
        No relatives with a history of breast cancer
    Physical Findings:
        none
    Mammographic Findings:
        Indirect Findings:
```

-continued

```
    Developing Density: present
    Direct Findings:
       Mass: present
       Mass Characteristics Noted:
          Tumor Location: upper outer quadrant
          Mass Margin: spiculated margin
          Halo Sign: absent
       Calcifications: absent
Breast Cancer Diagnosis Results:
    Initial likelihood of breast cancer is nn out of nnn.
    Evidence "Age = 45" increases the likelihood to n.
    Evidence "Age Menstruation Started = 13" increases the likelihood
       from n to m.
    Evidence "No Children" increases the likelihood from m to p.
    Evidence "No Relatives with a History of Breast Cancer" decreases
       the likelihood from p to a.
    Evidence "Developing Density Present" increases the likelihood
       from a to b.
    Evidence "Mass located in the upper outer quadrant" does not affect
       the likelihood.
    Evidence "Mass Margin = Spiculated" increases likelihood from b to
       i.
    Evidence "Halo Sign Absent" increases likelihood from i to x.
    The cumulative affect of all evidence entered for patient Jane Doe
       increases an initial likelihood nn to x, a factor of y.
```

Re-initialize the Network (BNReInitNetwork( ))

After an evidence vector has been scanned and the associated network updating is completed, another evidence vector may be propagated, but the network must first return to its initial configuration. The system has stored the initial joint vectors and prior unconditional vectors calculated during system startup initialization. These vectors are used to put the system in the initial configuration necessary.

The system puts itself into a re-initialized state. All joint probability and prior probability vectors are recalculated to an initial state, i.e., the conditional vectors are used to recalculate the joint vectors, and from the joint vectors the initial prior probability vectors are calculated. The previous prior probability vectors are set to the initial (current) prior probability vector. All flags that track evidence, node updating, and clique updating are reset to their default states, indicating the system has not received any user-entered evidence.

```
for all nodes N_i,
    reset N_i's previous prior probability vector
    reset N_i's current prior probability vector
for all nodes N_i's no parent nodes,
       reset node N_i's current prior probability vector to initial
          values
for all nodes N_i,
    recalculate current prior probability vectors:
    unmark any nodes N_i marked for receiving evidence flags,
    unmark any nodes N_i marked updated
    unmark any cliques C_i marked updated
    set root clique to Clique 0
    recalculate joint and prior probability vectors for all nodes N_i,
       BNInitNetwork()
for all nodes N_i,
    set nodes N_i's current prior probability vectors to calculated values
    set nodes N_i's previous prior probability vectors to current prior
       probability vectors
    reset node flags, received_evidence and updated_flag via a call to,
       unmark any nodes N_i marked for receiving evidence flags,
       unmark any nodes N_i marked updated
       unmark any cliques C_i marked updated
```

Initialize the Network (BNInitNetwork( ))

Certain system initialization tasks are done at system startup and when a new patient case is to be calculated. All cliques $C_i$ are traversed, starting at the root clique, and each clique $C_i$ has its joint and prior probability vectors re-initialized.

```
for all cliques C_i,
    if clique C_i is invalid, return
    calculate clique C_i's joint vector, BNCalcJointProbs()
    for each member node N_i in clique C_i, calculate prior probability
       vector, BNCalcPriorProbs()
    mark clique updated
    if clique C_i previous link is valid
    if clique C_i is not marked updated, re-initialize clique,
       BNInitNetwork()
    if clique C_i next link of clique is valid,
       if clique C_i is not marked updated, re-initialize clique,
          BNInitNetwork()
```

Calculate Joint Probability Vectors (BNCalcJointProbs())

Initial joint probability vectors are calculated at initial system startup and when a new patient case is to be propagated through the network. The calculation is done at each clique, $C_i$, starting at the clique marked as the root clique (Clique 0). The clique tree is traversed based on the ordering of the clique links at each clique $C_i$. At each clique $C_i$, the conditional vector is multiplied by the product of the non-base nodes of the clique.

```
for a clique C_i of nodes X_0, ... , X_{m-1},
    calculate joint vector p(x_0,x_1, ... x_{m-1})
       p(x_0,x_1, ... x_{m-1})=p(x_0 | x_1, ... ,x_{m-1}) · p(x_1) ... (p(x_{m-1}))
```

The system would then be ready to process another evidence vector.

Although a preferred embodiment of this invention has been described above, those skilled in the art could make numerous alterations to the disclosed embodiment without departing from the spirit or scope of this invention. It is intended that all matter contained in the above description or shown in the accompanying figures shall be interpreted as illustrative only and not limiting.

I claim:

1. A method of diagnosing breast cancer comprising the steps of
   generating an inference engine;
   calculating probability data using conditional and non-conditional values;
   receiving patient-specific evidence;
   propagating said patient-specific evidence through said inference engine to update said probability data and thereby determine a breast cancer diagnosis; and
   reporting said breast cancer diagnosis.

2. The method of claim 1, wherein said generating an inference engine step further comprises generating an inference engine that uses Bayesian network theory and techniques.

3. The method of claim 2, wherein said receiving patient-specific evidence step further comprises acquiring evidence in a single-patient mode.

4. The method of claim 2, wherein said receiving patient-specific evidence step further comprises acquiring evidence in a multiple-patient mode.

5. The method of claim 3 or 4, wherein said receiving patient-specific evidence step further comprises entering evidence through a user interface selected from the group consisting of graphical user interfaces, hypertext documents, database forms, and batch files.

6. A method of diagnosing breast cancer comprising the steps of generating a Bayesian network having a first predetermined number of nodes and a second predetermined number of cliques;

initializing said Bayesian network;

creating an evidence vector;

initializing said evidence vector;

receiving patient-specific evidence;

updating said evidence vector using said patient-specific evidence;

propagating said updated evidence vector through said Bayesian network to determine a breast cancer diagnosis;

estimating an influence of each piece of patient-specific evidence on said breast cancer diagnosis;

reporting said breast cancer diagnosis; and reporting said estimated influence.

7. A method of diagnosing breast cancer using an inference engine, comprising the steps of (a) generating a Bayesian network having a predetermined number of member components;

(b) initializing said Bayesian network;

(c) creating an evidence vector;

(d) initializing said evidence vector;

(e) computing a posterior probability value of breast cancer by propagating said evidence vector through said network;

(f) customizing said evidence vector by specifying observed evidence values for a specific patient;

(g) verifying that said customized evidence vector is correct;

(h) updating said posterior probability value of breast cancer by propagating said customized evidence vector through said network; and (i) outputting said posterior probability value.

8. The method of claim 7, wherein said generating a Bayesian network step further comprises creating twenty-six nodes as said member components, and organizing said nodes into a tree of twenty-one cliques comprising groups of said nodes.

9. The method of claim 8, wherein said initializing said Bayesian network step further comprises assigning initial values to each of said twenty-six nodes and said twenty-one cliques.

10. The method of claim 8, wherein said twenty-six nodes comprise five nodes without parents and twenty-one nodes with parents, and wherein said initializing said Bayesian network step further comprises (a) assigning initial prior probability vectors to all nodes without parents;

(b) assigning initial conditional probability vectors to all nodes with parents;

(c) calculating initial joint probability vectors for each of said nodes;

(d) storing said initial joint probability vectors;

(e) calculating new prior probability vectors for each of said nodes with parents using said initial joint probability vectors; and (f) storing said new prior probability vectors.

11. The method of claim 8, wherein said initializing said Bayesian network step further comprises (a) initializing each of said twenty-six nodes with the following information: number of possible states, textual name of node for reports, node number for identification, number of parent nodes, number of children nodes, size of an associated joint vector, children nodes, parent nodes, clique node is a member of, prior probability vector, conditional probability vector; and (b) initializing each of said twenty-one cliques with the following information: number of node members in said clique, clique number for identification, root clique indicator, number of links to other cliques, list of links to other cliques, number of common nodes, member nodes referenced by node number, common nodes referenced by node number, and base node.

12. The method of claim 8, wherein said creating an evidence vector step further comprises creating an evidence vector containing an entry corresponding to each of said twenty-six nodes.

13. The method of claim 12, wherein said twenty-six nodes comprise five nodes without parents and twenty-one nodes with parents, and wherein said updating said posterior probability value of breast cancer step further comprises (a) selecting an observed evidence value from said evidence vector;

(b) calculating new joint probability vectors for each of said cliques comprising said node corresponding to said selected observed evidence value;

(c) storing said new joint probability vectors;

(d) calculating new prior probability vectors for each of said nodes with a parent using said new joint probability vectors; and (e) storing said new prior probability vectors.

14. The method of claim 8, wherein, in said step (h) of claim 7, said propagating said customized evidence vector further comprises marking one of said cliques as a root clique, and traversing said clique tree starting at said root clique.

15. The method of claim 13, further comprising the steps of (a) storing said posterior probability value following step (e) of claim 5;

(b) storing said posterior probability value following step (h) of claim 5;

(c) storing said selected observed evidence value;

(d) calculating a difference between said posterior probability value stored in step (a) of this claim and said posterior probability value stored in step (b) of this claim;

(e) determining a reason for said difference calculated in step (d) of this claim using said stored selected observed evidence value; and (f) outputting said reason.

16. A method of diagnosing breast cancer comprising the steps of generating a Bayesian network having twenty-six nodes and twenty-one cliques;

initializing said Bayesian network;

creating an evidence vector;

initializing said evidence vector;

receiving patient-specific evidence;

updating said evidence vector using said patient-specific evidence;

propagating said updated evidence vector through said Bayesian network to determine a breast cancer diagnosis;

estimating an influence of each piece of patient-specific evidence on said breast cancer diagnosis;

reporting said breast cancer diagnosis; and reporting said estimated influence.

17. The method of claim 16, wherein said receiving patient-specific evidence step further comprises receiving patient-specific evidence concerning at least one of the following factors: age in years, age of menarche, age of first live birth, number of first order relatives with cancer, previous biopsy at site, breast pain, nipple discharge, palpable mass, developing density in breast, asymmetry in breast, dilated duct in breast, architectural distortion, halo sign, tumor location by quadrant, mass size, mass margin, mass density, calcification shape, calcification density, calcification number, calcification size, calcification cluster shape, and calcification arrangement.

18. The method of claim 16, wherein said receiving patient-specific evidence step further comprises the following:

receiving demographic factors;

receiving physical examination findings; and receiving mammographic findings.

19. The method of claim 18, wherein said receiving mammographic findings step comprises receiving direct mammographic findings and receiving indirect mammographic findings.

20. The method of claim 18, wherein said receiving demographic factors step comprises receiving information concerning at least one of the following factors: age in years, age of menarche, age of first live birth, number of first order relatives with cancer, and previous biopsy at site.

21. The method of claim 20, wherein said receiving physical examination findings step comprises receiving information concerning at least one of the following factors: breast pain, nipple discharge, and palpable mass.

22. The method of claim 21, wherein said receiving mammographic findings step comprises receiving information concerning at least one of the following factors: mass margin, mass density, mass size, halo sign, tumor location by quadrant, calcification cluster shape, calcification number, calcification shape, calcification density, calcification arrangement, calcification size, architectural distortion, asymmetry in breast, developing density in breast, and dilated duct in breast.

23. The method of claim 21, wherein said receiving mammographic findings step comprises receiving direct mammographic findings and receiving indirect mammographic findings.

24. The method of claim 23, wherein said receiving direct mammographic findings step comprises receiving information concerning at least one of the following factors: mass margin, mass density, mass size, halo sign, tumor location by quadrant, calcification cluster shape, calcification number, calcification shape, calcification density, calcification arrangement, and calcification size; and wherein said receiving indirect mammographic findings step comprises receiving information concerning at least one of the following factors: architectural distortion, asymmetry in breast, developing density in breast, and dilated duct in breast.

* * * * *